US008912315B2

(12) United States Patent
Hirai et al.

(10) Patent No.: US 8,912,315 B2
(45) Date of Patent: Dec. 16, 2014

(54) PURKINJE CELL-TROPIC VIRAL VECTOR

(75) Inventors: Hirokazu Hirai, Ishikawa (JP); Takashi Torashima, Ishikawa (JP)

(73) Assignee: Japan Science and Technology Agency, Saitama (JP)

( * ) Notice: Subject to any disclaimer, the term of this patent is extended or adjusted under 35 U.S.C. 154(b) by 1320 days.

(21) Appl. No.: 12/224,827

(22) PCT Filed: Mar. 7, 2007

(86) PCT No.: PCT/JP2007/055017
§ 371 (c)(1),
(2), (4) Date: Jan. 28, 2009

(87) PCT Pub. No.: WO2007/105744
PCT Pub. Date: Sep. 20, 2007

(65) Prior Publication Data
US 2010/0146649 A1    Jun. 10, 2010

(30) Foreign Application Priority Data

Mar. 8, 2006  (JP) ................. 2006-062192
Jul. 20, 2006  (JP) ................. 2006-198398

(51) Int. Cl.
*C12N 7/00* (2006.01)
*C12N 7/02* (2006.01)
*C12N 15/85* (2006.01)
*A61K 48/00* (2006.01)
*C12N 15/86* (2006.01)
*A61K 38/17* (2006.01)

(52) U.S. Cl.
CPC ............ *C12N 15/85* (2013.01); *A61K 48/0058* (2013.01); *C12N 15/86* (2013.01); *A61K 38/1709* (2013.01); *A61K 38/177* (2013.01); *C12N 2740/13032* (2013.01); *C12N 2740/13043* (2013.01); *C12N 2800/108* (2013.01); *C12N 2820/60* (2013.01); *C12N 2830/008* (2013.01); *C12N 2830/60* (2013.01)
USPC ....... 536/24.1; 424/93.1; 424/93.2; 424/93.6; 435/320.1; 514/44

(58) Field of Classification Search
USPC .............. 424/93.1, 93.2, 93.6; 435/320.1; 514/44; 536/24.1
See application file for complete search history.

(56) References Cited

U.S. PATENT DOCUMENTS

| 6,515,197 B1 | 2/2003 | Pulst et al. | |
|---|---|---|---|
| 2004/0073960 A1* | 4/2004 | Yoshihara | ........................ 800/8 |
| 2004/0204368 A1 | 10/2004 | Ohmoto et al. | |

FOREIGN PATENT DOCUMENTS

| JP | 2002-543796 | 12/2002 |
|---|---|---|
| JP | 2004-506444 | 3/2004 |
| JP | 2006-50956 | 2/2006 |
| JP | 2006-504651 | 2/2006 |
| WO | 00/68414 | 11/2000 |
| WO | 02/096892 | 12/2002 |
| WO | 2004/007501 | 1/2004 |

OTHER PUBLICATIONS

International Search Report issued Jun. 26, 2007 in the International (PCT) Application PCT/JP2007/055017 of which the present application is the U.S. National Stage.
Torashima, T. et al., "In vivo transduction of murine cerebellar Purkinje cells by HIV-derived lentiviral vectors", *Brain Research*, (2006), 1082(1): 11-22.
Torashima T. et al., "Exposure of lentiviral vectors to subneutral pH shifts the tropism from Purkinje cell to Bergmann glia", *European Journal of Neuroscience*, (2006), 24(2): 371-380.
Hirai, Hirokazu, "Production of HIV-derived lentiviral vectors with high tropism for neurons", *Experimental Medicine*, (2006), 24(19): 2997-3001. (English Translation).
Kurschner, C. et al., "The *maf* Proto-oncogene Stimulates Transcription from Multiple Sites in a Promotor That Directs Purkinje Neuron-Specific Gene Expression", *Molecular and Cellular Biology*, (1995), 15(1): 246-254.
Kido, H. et al., "Host cellular proteases which determine the susceptibility and organ tropism of human influenza virus infection", *The Japanese Society on Thrombosis and Hemostasis*, (2004), 15(4): 362-365.
Ooka, S. et al., "RNA virus to Tropism to Byogensei", *Protein, nucleic acid and enzyme*, (2003), 48:4: 517-523.
Tashiro, M. et al., "Tryptase Clara, an Activating Protease for Sendai Virus in Rat Lungs, is Involved in Pneumopathogenicity", *Journal of Virology*, (1992), 66(12): 7211-7216.
Haag, L. et al., "Acid-induced movements in the glycoprotein shell of an alphavirus turn the spikes into membrane fusion mode", *The EMBO Journal*, (2002), 21(17): 4402-4410.
Kaemmerer, W. F. et al., "In Vivo Transduction of Cerebellar Purkinje Cells Using Adeno-Associated Virus Vectors", *Molecular Therapy*, (2000), 2(5): 446-457.
Agudo, M. et al., "Highly Efficient and Specific Gene Transfer to Purkinje Cells In Vivo Using a Herpes Simplex Virus I Amplicon", *Human Gene Therapy*, (2002), 13:665-674.
Bouktouche, F. et al., "Retinoid-Related Orphan Receptor α Controls the Early Steps of Purkinje Cell Dendritic Differentation", *The Journal of Neuroscience*, (2006), 26(5): 1531-1538.
Morizono, K. et al., "Transient low pH treatment enhances infection of lentiviral vector pseudotypes with a targeting Sindbis envelope", *Virology*, (2006), 355: 71-81.

* cited by examiner

*Primary Examiner* — Kevin Hill
(74) *Attorney, Agent, or Firm* — Wenderoth, Lind & Ponack, L.L.P.

(57) ABSTRACT

The present invention relates to a Purkinje cell-tropic viral vector in which a modified L7 promoter and a therapeutic gene are operably linked to a virus-based plasmid vector.

19 Claims, 17 Drawing Sheets
(8 of 17 Drawing Sheet(s) Filed in Color)

Fig. 4
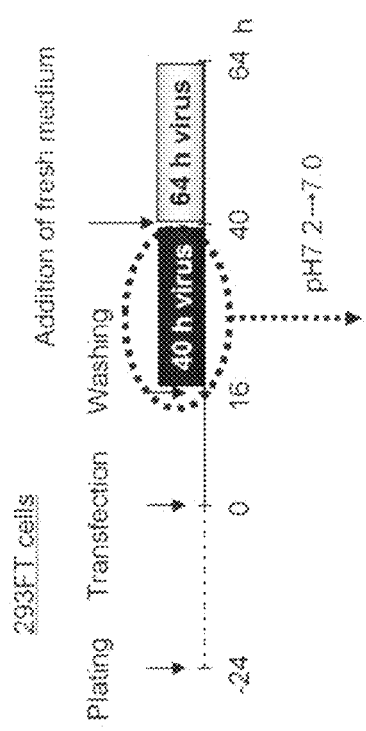
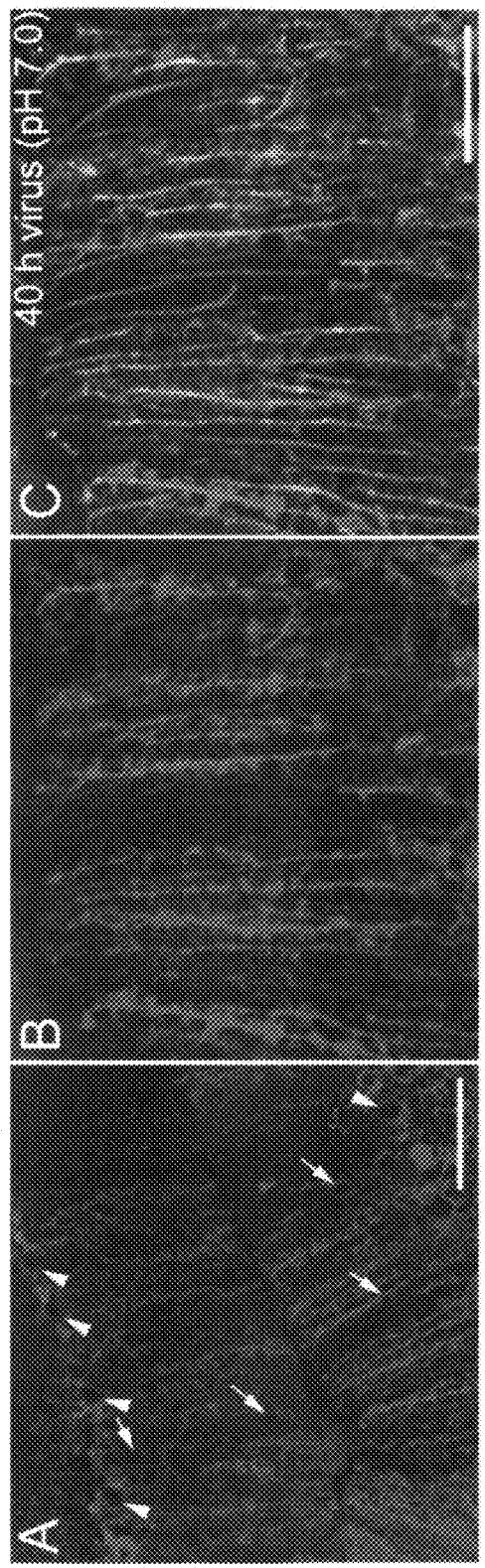

Fig. 10
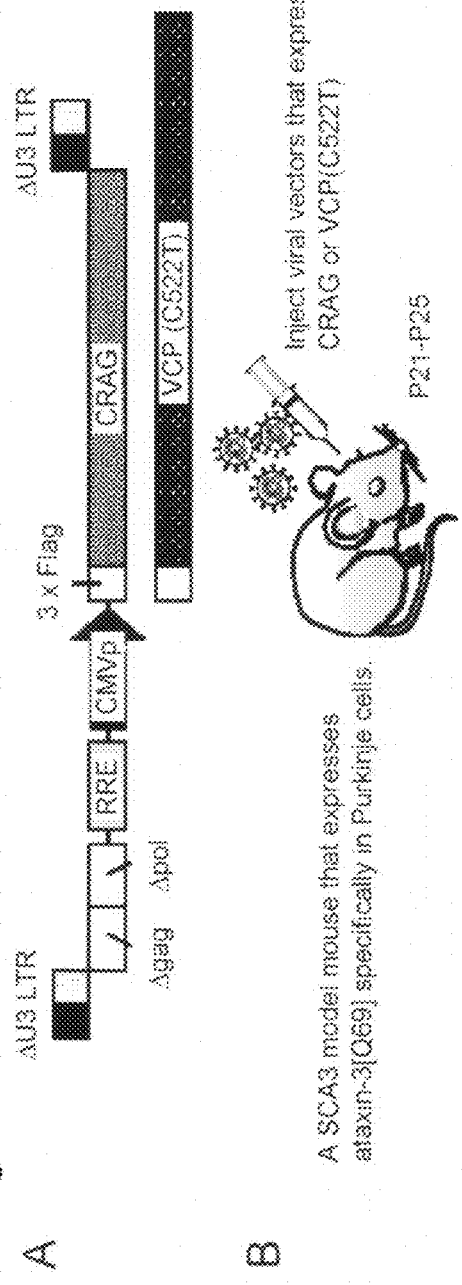
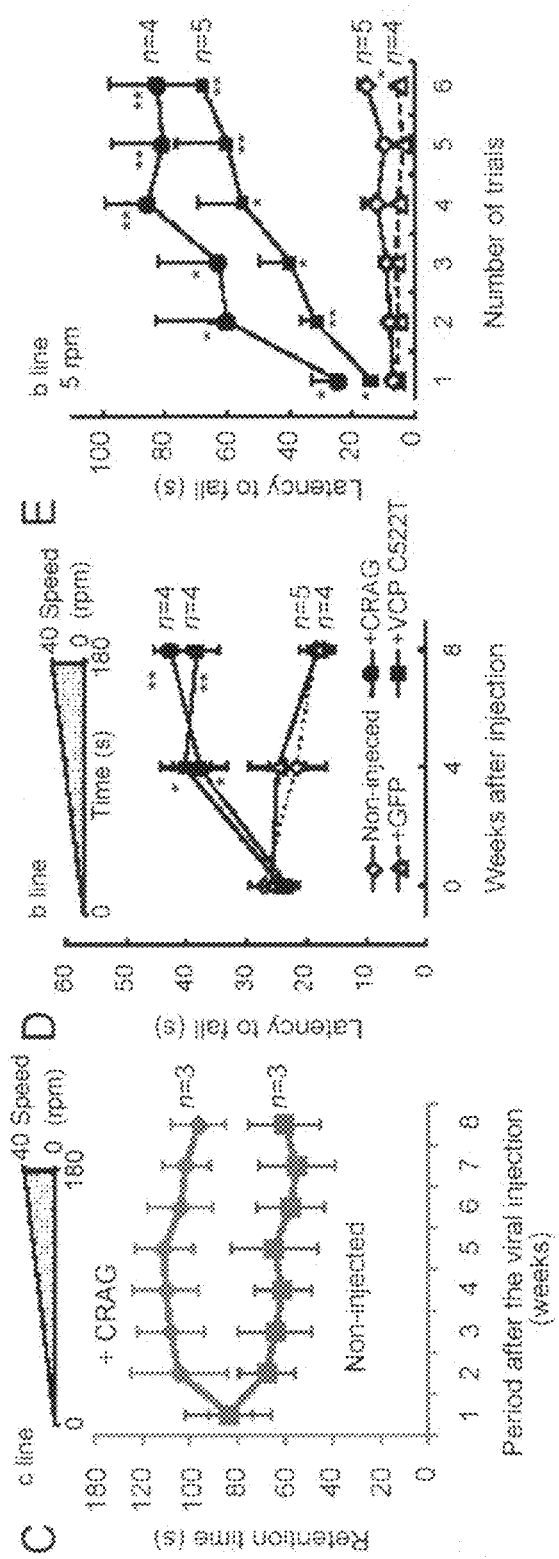

Fig. 14
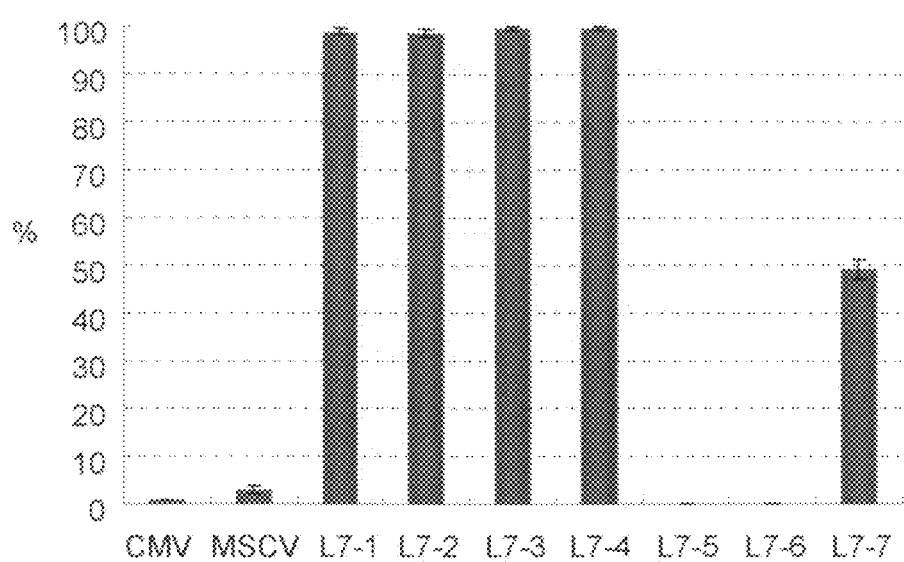
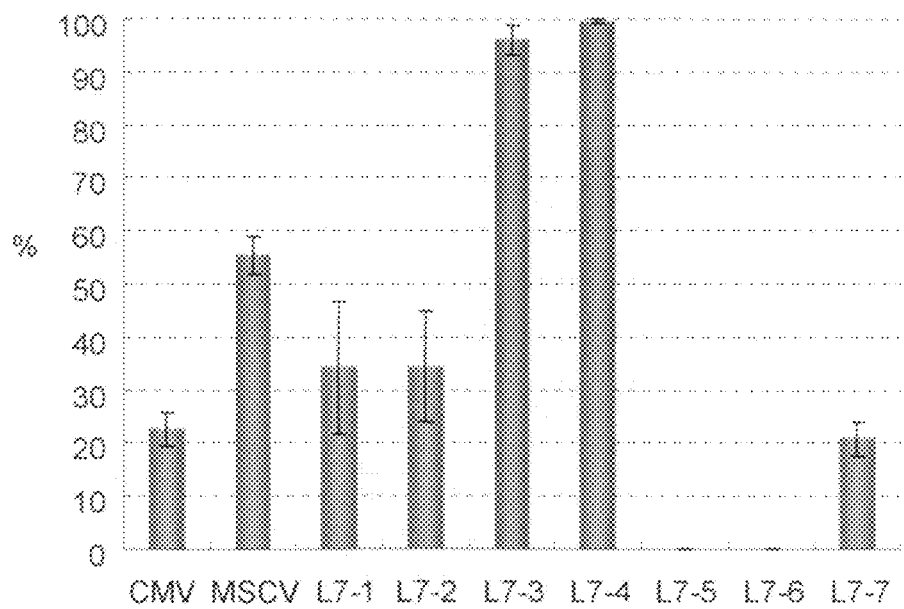

Fig. 17
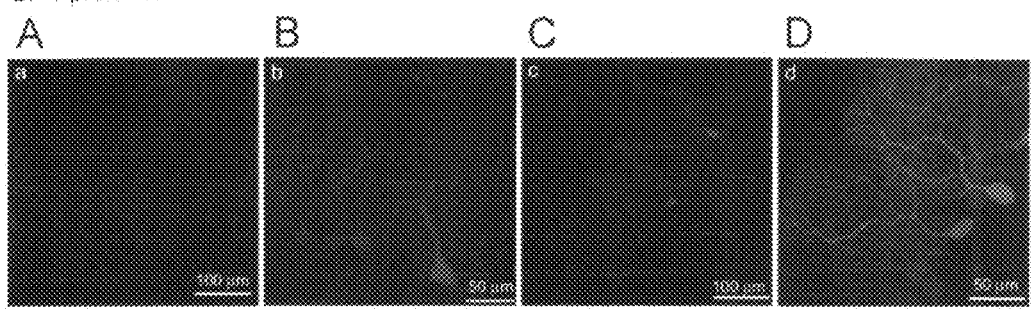
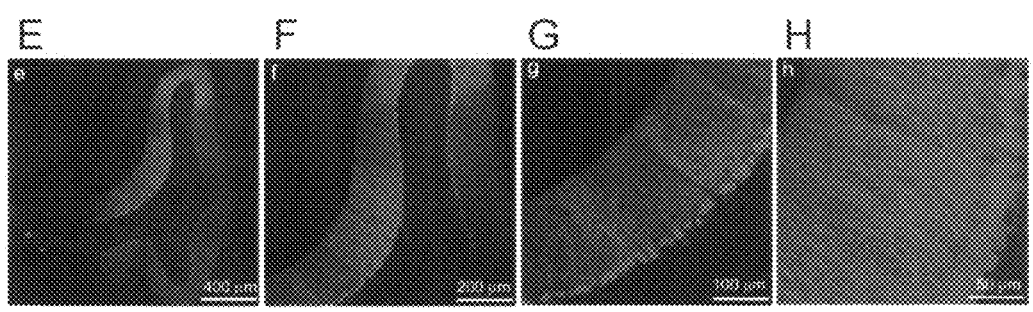

PURKINJE CELL-TROPIC VIRAL VECTOR

TECHNICAL FIELD

The present invention relates to a Purkinje cell-tropic viral vector obtained using a modified L7 promoter.

BACKGROUND ART

The cerebellum plays an important role in motor coordination, such as walking, in which plural muscles are involved. Damage of cerebellum results in unsuccessful regulation of motor coordination and failed smooth movement. Motor commands from the cerebral cortex are transmitted through the brain stem to the spinal cord and muscles, while these commands are also transmitted from the brain stem (pons) via mossy fibers to the cerebellar cortex. The signals transmitted via mossy fibers are input to granule cells which are cerebellar cortex neurons. Then, the granule cells transmit the signals to Purkinje cells via their axons, parallel fibers.

One Purkinje cell forms 100,000 or more synapses with the parallel fibers. The Purkinje cells integrate input information therefrom and output the information to the cerebellar nuclei located in the deep region of the cerebellum. The Purkinje cells, the sole output neurons from the cerebellar cortex, play a very important role in the cerebellum. However, they are fragile and are easily damaged due to cerebellar hemorrhage, injury, cerebellar tumor, or inherited neurodegenerative disease.

With the developments in genomics in recent years, the human and mouse complete genome sequences have been determined. Life science research is now headed for the elucidation of roles of identified genes. An approach which involves introducing a wild-type or mutant gene to neurons and examining its influence is very effective from the viewpoint of research in the neuroscience field. Such gene transfer to neurons is also getting attention from the viewpoint of clinical application as gene therapies.

However, the gene transfer to neurons is difficult, because they are nondividing cells. Among others, gene transfer to Purkinje cells is exceedingly difficult. Prior to 2000, successful cases of efficient gene transfer to Purkinje cells were not reported. Recent progress in the development of viral vectors has permitted efficient gene transfer to Purkinje cells. Nevertheless, only 4 articles have been reported so far (Non-Patent Documents 1 to 4: Agudo M., Trejo J. L., Lim F., Avila J., Torres-Aleman I., Diaz-Nido J. & Wandosell F. (2002) Highly efficient and specific gene transfer to Purkinje cells in vivo using a herpes simplex virus I amplicon. Hum. Gene Ther., 13, 665-674; Alisky J. M., Hughes S. M., Sauter S. L., Jolly D., Dubensky T. W. Jr., Staber P. D., Chiorini J. A. & Davidson B. L. (2000) Transduction of murine cerebellar neurons with recombinant FIV and AAV5 vectors. Neuroreport, 11, 2669-2673; Kaemmerer W. F., Reddy R. G., Warlick C. A., Hartung S. D., McIvor R. S. & Low W. C. (2000) In vivo transduction of cerebellar Purkinje cells using adeno-associated virus vectors. Mol. Ther., 2, 446-457; and Xia H., Mao Q., Eliason S. L., Harper S. Q., Martins I. H., Orr H. T., Paulson H. L., Yang L., Kotin R. M. & Davidson B. L. (2004) RNAi suppresses polyglutamine-induced neurodegeneration in a model of spinocerebellar ataxia. Nat. Med., 10, 816-820).

Efficient gene transfer to Purkinje cells requires the use of vectors based on viruses, such as a lentivirus or adeno-associated virus, which have high affinity for neurons. For information, an adenovirus, a herpesvirus, an adeno-associated virus, and a feline immunodeficiency virus-derived lentivirus have been used in the gene transfer to Purkinje cells in the previous reports.

A wild-type lentivirus infects only lymphocytes having CD4 receptors. Therefore, lentiviral vectors currently used have their envelope proteins substituted by a vesicular stomatitis virus glycoprotein (VSV-G) such that they also infect neurons. This VSV-G has the ability to bind to phospholipid (phosphatidylserine) serving as a component of cell membranes and therefore nonspecifically infects non-neuronal cells such as glial cells and vascular endothelial cells. Moreover, in the cerebellum, the lentivirus also infects stellate cells, basket cells, Golgi cells, and Bergmann glia, in addition to Purkinje cells.

As described above, an adeno-associated viral or lentiviral vector has the ability to introduce a foreign gene to neurons and express the gene. However, these viral vectors have a limitation of the size of a gene which can be expressed, due to the problems of their packaging abilities. The size of a gene which can be expressed is allegedly 4 kb and 8 kb, including promoter regions, for adeno-associated viral and lentiviral vectors, respectively. However, this is a theoretical value. Lentiviral vector plasmids are variously modified for increasing safety. Therefore, gene size to be expressed is often limited to around 5 kb, though it differs depending on vector plasmids used.

On the other hand, an L7 promoter, which is active specifically in Purkinje cells, has been utilized in the production of transgenic mice expressing a foreign gene only in Purkinje cells. However, the L7 promoter is as large as approximately 3 kb in full length and has a large limitation of the size of a foreign gene to be expressed, when inserted in an adeno-associated viral or lentiviral vector for use. Moreover, its promoter activity is much lower than that of a nonspecific promoter such as a CMV or MSCV promoter.

Efficient and specific gene transfer to cerebellar Purkinje cells has been achieved only by a method which involves producing transgenic mice. However, specific and highly efficient gene transfer to Purkinje cells using viral vectors will permit various studies never before achieved and largely contribute to developments in studies focused on the cerebellum. Moreover, such gene transfer is also expected to be applied to gene therapies for Purkinje cell-affecting diseases such as spinocerebellar ataxia.

Moreover, infections including bovine spongiform encephalopathy have presented large problems in recent years, when viral vectors are used in humans for gene therapies. This is because current protocols require adding bovine serum to a medium during virus generation. Thus, if a viral vector that achieves highly efficient gene transfer to Purkinje cells can be generated without the use of serum, its clinical application is expected to be more expanded.

SUMMARY OF THE INVENTION

An object of the present invention is to provide a viral vector that has high affinity for cerebellar Purkinje cells and selectively infect Purkinje cells for gene expression.

The present inventors have previously conducted experiments of gene transfer to the cerebellum using a human immunodeficiency virus-derived lentiviral vector on which no gene transfer to the cerebellum had been reported, and have found that the Purkinje cell selectivity of the virus is drastically reduced merely due to the slight shift of culture medium pH to the acidic zone during virus generation, and that the selectivity of the virus for Purkinje cells differs depending on the lot of serum added to the culture medium, and hence, a certain ingredient in serum participates in the maintenance of Purkinje cell selectivity.

Based on the findings, the present inventors have further made the following hypotheses and have attempted to demonstrate them:

(1) since the selectivity of the virus for Purkinje cells varies depending on culture medium pH, a pH-sensitive enzyme, probably, protease released from host cells modifies viral proteins (particularly, glycoproteins present on the viral envelope), resulting in reductions in the selectivity of the virus for Purkinje cells; and (2) serum contains a substance that inhibits protease activities, and therefore, the modification of glycoproteins on the viral envelope is suppressed, so that the selectivity for Purkinje cells is maintained.

Indeed, in Sendai or influenza viruses, it has been known that glycoproteins on the envelopes are cleaved by protease, resulting in changes in infectivity for cells. In addition, the experimental results by the present inventors have supported the hypotheses. A vector having high affinity for Purkinje cells could be obtained by adding a protease inhibitor to a culture medium during virus generation. However, the viral vector also infects approximately 10 to 20% of all cells other than Purkinje cells and induces gene expression. Thus, a promoter inserted in the viral vector was changed from a nonselective CMV or MSCV promoter to an L7 promoter for studies such that gene expression was completely induced only in Purkinje cells. Since a conventional L7 promoter has 3 kb in length, promoters having various lengths shorter than this 3 kb were prepared and inserted to viral plasmids. Viral vectors were obtained using these viral plasmids and injected to the cerebellums of mice for studies in vivo. As a result, a viral vector inserting therein a modified L7 promoter having the nucleotide sequence shown in SEQ ID NO: 3 or 4 was observed to cause gene expression only in Purkinje cells, and the expression level was also demonstrated to be much higher than that achieved by the conventional L7 promoter.

Specifically, the present invention relates to a cerebellar Purkinje cell-tropic vector in which a modified L7 promoter having the nucleotide sequence shown in SEQ ID NO: 3 or 4 and a foreign gene are operably linked to a virus-based vector plasmid.

The virus-based vector plasmid used include, for example, adenovirus-, adeno-associated virus-, retrovirus-, herpesvirus-, Sendai virus-, and lentivirus-based vector plasmids. For the effect of a protease inhibitor, it is preferred that a glycoprotein on the envelope is VSV-G.

It is preferred that the vector produces a viral protein, particularly, a glycoprotein present on the viral envelope, in a state with substantially no degradation.

When the glycoprotein present on the viral envelope is in a state with substantially no degradation, the vector can be obtained by generating a virus in a host cell in a culture medium comprising a protease inhibitor. A protease inhibitor having a cathepsin K inhibitory activity (cathepsin K inhibitor or cathepsin inhibitor) is preferable as the protease inhibitor.

It is preferred that the culture medium during virus generation is kept at pH 7.2 to 8.0.

Moreover, from the viewpoint of safety such as infection prevention, it is preferred that the culture medium is serum-free.

The present invention also provides a cerebellar Purkinje cell-tropic vector in which a foreign gene is operably linked to a lentiviral vector plasmid, characterized in that the vector produces a viral protein, particularly, a glycoprotein present on the viral envelope, in a state with substantially no degradation. When the glycoprotein present on the viral envelope is in a state with substantially no degradation, the vector can be obtained by the method described above.

The foreign gene inserted into the viral vector include, for example, a therapeutic gene for Purkinje cell-affecting disease and a gene responsible for the disease (disease gene). The vector of the present invention comprising such a gene inserted thereinto can be used in the gene therapies for Purkinje cell-affecting disease and the production of model animals of the disease.

Specific examples of the therapeutic gene can include genes encoding molecular chaperones including GTPase CRAG, ubiquitin chain assembly factor E4B (UFD2a), ATPase VCP/p97, HDJ-2, HSDJ, and BiP, apoptosis suppressors including YAPdeltaC, endoplasmic reticulum protein degradation-promoting molecules including ER degradation enhancing alpha-mannosidase-like protein (EDEM), ER sensor molecules (endoplasmic reticulum stress transducers) including CREB/ATF family members OASIS, IRE1, PERK, and ATF6, sphingomyelinase, AT-mutated (atm), Reelin, Bcl-2, neprilysin, BDNF, and NGF, and siRNAs for genes encoding ataxin-1, ataxin-2, ataxin-3, voltage-dependent calcium channel α1a subunit, and PKCγ.

Alternatively, specific examples of the disease gene can include genes with an abnormally expanded CAG repeat that encode ataxin-1, ataxin-2, ataxin-3, huntingtin, and voltage-dependent calcium channel α1a subunit, and a gene encoding PKCγ having a mutation.

The present invention also provides a pharmaceutical composition for the treatment of cerebellar Purkinje cell-affecting disease comprising the cerebellar Purkinje cell-tropic vector.

The cerebellar Purkinje cell-affecting disease can include polyglutamine disease including spinocerebellar ataxia and Huntington disease, Niemann-Pick disease, ataxia-telangiectasia, autism, Alzheimer's disease, fetal alcohol syndrome (FAS), alcoholism, and age-related cerebellar ataxia.

The present invention also provides a non-human mammal comprising the vector of the present invention introduced thereinto. Particularly, a non-human mammal that comprises a causative gene of Purkinje cell damage (a gene with an abnormally expanded CAG repeat that encods ataxin-1, ataxin-2, ataxin-3, huntingtin, or voltage-dependent calcium channel α1a subunit, or a gene encoding PKCγ having a mutation) introduced thereinto and expresses the gene specifically in Purkinje cells can be used as a model animal of the cerebellar Purkinje cell-affecting disease.

The present invention also provides a method for preparing a Purkinje cell-tropic viral vector, comprising: operably linking a foreign gene to a lentiviral plasmid vector; introducing the plasmid vector into a host cell; and culturing the cell in a culture medium comprising a protease inhibitor to produce a virus. Alternatively, the present invention provides a method for preparing a Purkinje cell-tropic viral vector, comprising: operably linking a modified L7 promoter having the nucleotide sequence shown in SEQ ID NO: 3 or 4 and a foreign gene to a virus-based vector plasmid; and culturing the cell in a culture medium comprising a protease inhibitor to produce a virus.

Furthermore, the present invention also provides a culture medium for preparing a Purkinje cell-tropic viral vector comprising a substance having a cathepsin K inhibitory activity and a kit for preparing a Purkinje cell-tropic viral vector comprising, as a component, such a culture medium (a substance having a cathepsin K inhibitory activity and a cell culture medium, or a cell culture medium comprising a substance having a cathepsin K inhibitory activity).

The modified L7 promoter used in the present invention is approximately ⅓ the size of a conventional L7 promoter. Therefore, the size of a foreign gene which can be inserted in the vector is significantly increased. In addition, the modified L7 promoter has a much higher promoter activity than that of the conventional L7 promoter, when the same copy numbers are incorporated into chromosomes. Thus, the modified L7 promoter strongly induces the expression of the foreign gene located downstream thereof.

Accordingly, the present invention achieves selective and highly efficient gene expression in Purkinje cells which are most important in the cerebellum. Thus, in basic research, studies for elucidating, at a molecular level, mechanisms of motor learning or motor coordination controlled by the cerebellum are expected to make a large progress. Moreover, in clinical application including gene therapies, the present invention achieves gene transfer selective for Purkinje cells. Therefore, side effects associated with gene transfer or expression in other neurons or glial cells are expected to be reduced. Furthermore, in the present invention, the vector can be prepared without the use of bovine serum. Therefore, the present invention is free from the problems of infections such as bovine spongiform encephalopathy and is independent of the lot of serum. Thus, the Purkinje cell-tropic vector can be obtained stably.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 is a confocal scanning microscope image showing GFP expression in the molecular layer of the cerebellar cortex 1 week after injection of a virus harvested after adjustment of pH of a culture medium comprising a virus 40 hours after transfection to 7.0 by the addition of diluted hydrochloric acid. In A, GFP expression selective for Bergmann glia (arrows) is observed. Purkinje cells have no GFP expression and appear black (arrowheads). B is an enlarged image of A. C is an image of double staining with an antibody against GFAP which is a glial cell marker. GFP expression overlaps with GFAP distribution (red). The scale bar of A represents 100 μm, and the scale bar of B represents 50 μm.

FIG. 10A is a schematic diagram showing the structure of a proviral portion of a viral vector expressing Flag-tagged CRAG, or VCP (C522T) (cysteine at position 522 of VCP/p97 has been substituted by threonine). FIG. 10B is a schematic diagram showing the injection of this viral vector to the cerebellums of spinocerebellar ataxia type 3 model mice. FIG. 10C shows results of a rotarod test up to 8 weeks after injection of a CRAG-expressing virus to the cerebellum of the model mouse of the c line. FIG. 10D shows results of a rotarod test conducted 4 weeks and 8 weeks after injection of a GFP-, CRAG-, or VCP (C522T)-expressing virus to the cerebellum of the model mouse of the b line (in both FIGS. 10C and 10D, the rod initially stands still and is accelerated to a speed of 40 rpm after 180 seconds). FIG. 10E shows results of a rotarod test conducted at a constant speed (5 rpm) 8 weeks after injection of a GFP-, CRAG-, or VCP (C522T)-expressing virus to the cerebellum of the model mouse of the b line.

FIG. 11G shows the number of inclusions in the cerebellar cortex of each slice. FIG. 11H shows a molecular layer width in each slice.

FIG. 14 shows a GFP expression rate in Purkinje cells when various promoters are used. FIG. 14A shows the proportion of GFP-expressing Purkinje cells to all GFP-expressing cells: the number of GFP-expressing Purkinje cells/the number of GFP-expressing cells. FIG. 14B shows the proportion of GFP-expressing Purkinje cells to all Purkinje cells: the number of GFP-expressing Purkinje cells/the number of all Purkinje cells.

FIG. 17 shows results of gene transfer to the cerebellum in vivo. FIGS. 17A to 17D are respectively a fluorescence photograph of GFP expressed under the control of a conventional L7 promoter (L7-1) using a lentiviral vector. FIGS. 17C and 17D are respectively a photograph of immunostaining with an anti-GFP antibody (this enhances fluorescence). FIGS. 17E to 17H are respectively a fluorescence photograph of GFP in cerebellar Purkinje cells obtained using an L7-4 promoter.

Figure 1:
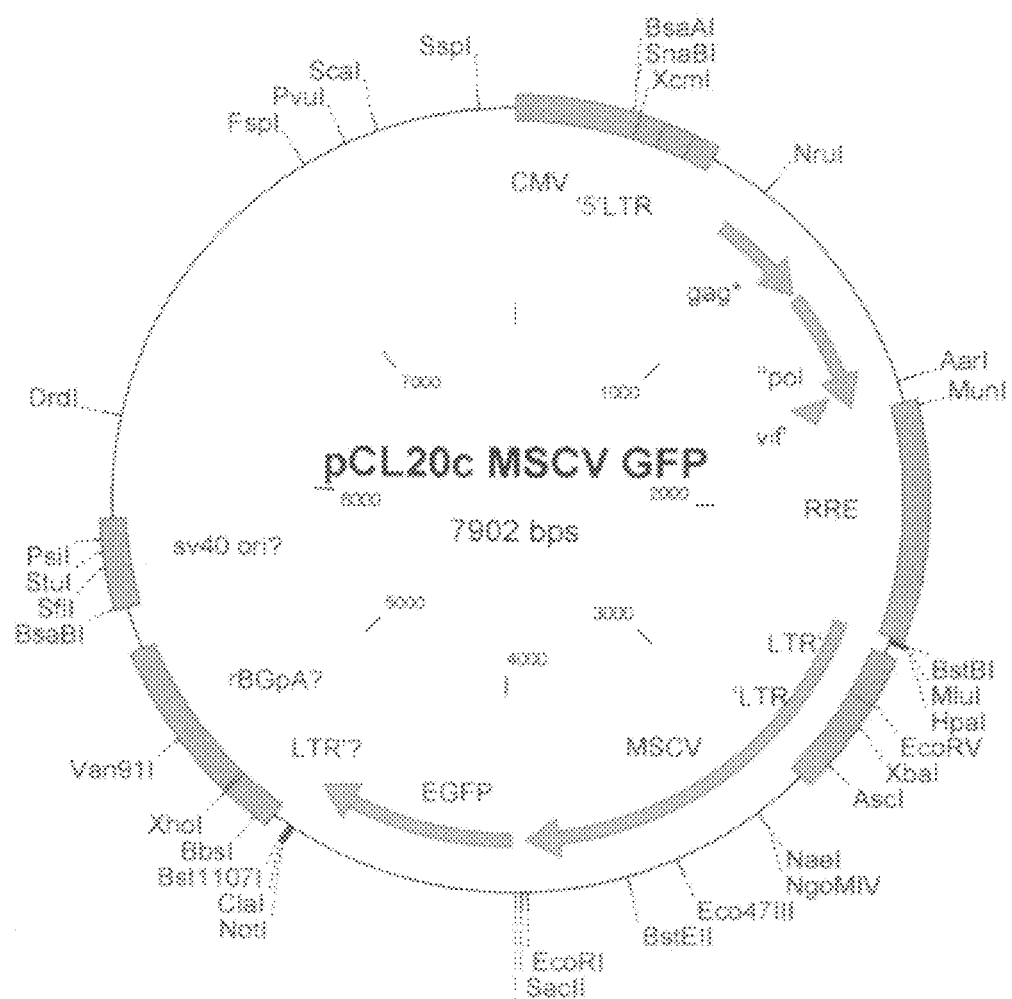
FIG. 1 shows the structure of pCL20c MSCV-GFP.

In the graphs shown in the drawings, $*p<0.05$, $p<0.01$, and $*p<0.001$ (ANOVA with least significance test).

The present specification encompasses the contents described in the documents of Japanese Patent Application Nos. 2006-062192 and 2006-198398 that serve as the basis of the priority of the present application.

BEST MODE FOR CARRYING OUT THE INVENTION

1. Purkinje Cell-Tropic Vector

A "Purkinje cell-tropic vector" according to the present invention (hereinafter, referred to as a "vector of the present invention") is a vector that has high affinity for cerebellar Purkinje cells and can achieve gene transfer specific for Purkinje cells. The vector of the present invention has higher selectivity for Purkinje cells than for other neurons, such as Bergmann glia, stellate cells, and basket cells, present in the cerebellum, or for glial cells.

In the vector of the present invention, a modified L7 promoter and a foreign gene are operably linked to a virus-based plasmid vector. Alternatively, an appropriate promoter and a foreign gene are operably linked to a lentiviral plasmid vector.

In this context, the virus-based plasmid vector includes adenovirus-, adeno-associated virus-, retrovirus-, herpesvirus-, Sendai virus-, and lentivirus-based plasmid vectors. Particularly, adeno-associated virus- and lentivirus-based plasmid vectors, which have high selectivity for Purkinje cells, are preferable. A lentiviral vector is most preferable.

The "lentivirus", which is one of RNA viruses having reverse transcriptase, can highly efficiently infect even non-dividing cells without cytokine stimulation and integrate the virus genome to a host chromosome. Therefore, the lentivirus-based vector is generally used as a vector for gene transfer to mammals. For example, a human immunodeficiency virus (HIV), a feline immunodeficiency virus (FIV), a simian immunodeficiency virus (SIV), an equine infectious anemia virus (EIAV), a caprine arthritis-encephalitis virus (CAEV), a maedi virus are known as lentiviruses. In general, vectors based on a human immunodeficiency virus, a feline immunodeficiency virus, and a simian immunodeficiency virus are used.

The viral particle of the lentivirus is composed of two plus-strand RNAs, core proteins (gag proteins) surrounding the RNAs, a matrix surrounding the core, and a lipid bilayer envelope further surrounding the matrix. The core contains reverse transcriptase, RNase H, integrase, and protease. The lipid bilayer is spiked with envelope proteins which are glycoproteins.

The proteins described above are intricately involved in viral infections and proliferation in hosts. Particularly, glycoproteins on the viral envelope are very important for the infectivity of the virus. In influenza viruses, it has been known that the cleavage of this glycoprotein with an enzyme alters their infectivity. HIV can infect only CD4-positive cells. In an HIV-based lentiviral vector, an envelope protein is substituted by a vesicular stomatitis virus glycoprotein (VSV-G) such that it can infect various kinds of cells. Thus, this VSV-G is presumably deeply involved in the Purkinje cell selectivity of the HIV-based lentiviral vector.

The lentiviral plasmid vector is usually composed of 2 to 4 components [packaging (packaging and REV plasmids), envelope, and vector]. Of them, the packaging plasmid supplies proteins necessary for the formation of a viral particle other than the envelope. A tat-rev region necessary for its replication is destroyed for preventing the replication in hosts. Alternatively, one of tat and rev is deleted, and the other region is transferred to another plasmid. The envelope plasmid supplies proteins necessary for envelope formation. HIV having the original envelope can infect only CD4-positive cells, as described above. Therefore, the envelope protein is substituted by VSV-G. The vector plasmid contains LTR, a packaging signal, and a primer-binding site necessary for reverse transcription. In a vector plasmid generally used, an LTR enhancer/promoter portion is deleted for enhancing safety. Instead, a foreign promoter such as a CMV promoter is inserted therein.

In a particularly preferable aspect of the present invention, a modified L7 promoter is used as the foreign promoter for appropriate and efficient foreign gene expression in Purkinje cells. This modified L7 promoter will be described in detail in a next paragraph.

In the vector of the present invention, a promoter, particularly, a modified L7 promoter, and a foreign gene are operably linked to a retroviral plasmid vector. In this context, the term "operably" means that the foreign gene is introduced into an infected host and appropriately expressed therein.

The "foreign gene" is a gene that is not originally carried by a retrovirus. A reporter gene (e.g., a GFP gene) for research as well as a therapeutic gene for gene therapies or a disease gene for the production of disease model mice is used. The "therapeutic gene" and the "disease gene" will be described later in detail.

For a virus generated by the vector of the present invention, it is preferred that its protein is in a state with substantially no degradation. Particularly, it is preferred that a glycoprotein VSV-G present on the viral envelope is in a state with substantially no degradation. This is because viral proteins play an important role in infections and proliferation in hosts, as described above. Indeed, the present inventors have demonstrated that the addition of a protease inhibitor to a culture medium for virus generation largely improves the selectivity of the virus for Purkinje cells. Here, the state with "substantially" no degradation does not strictly require that the degradation of the viral protein are absent by 100% from virus generation to use, but means that small inevitable degradation or modification that has no influences are accepted as long as the purpose (Purkinje cell tropism) is attained.

2. Modified L7 Promoter

The modified L7 promoter used in the present invention has been identified as a promoter region that maintains cell specificity with a length (1 kb) of approximately ⅓ that of a conventional cerebellar Purkinje cell-specific L7 promoter (SEQ ID NO: 1) having a length of 3 kb and also has a stronger activity.

Specifically, the modified L7 promoter of the present invention has the nucleotide sequence shown in SEQ ID NO: 3 (L7-3) or 4 (L7-4). However, the modified L7 promoter of the present invention is not limited to these sequences and also encompasses DNA which is capable of hybridizing under stringent conditions to DNA having a sequence complementary to the nucleotide sequence shown in SEQ ID NO: 3 or 4 as long as it has a base length (approximately 900 bp to 1500 bp) equivalent to that of the modified L7 promoter and has a Purkinje cell-specific promoter activity equivalent thereto. It will be understood that any fragment of consecutive 1006 bp to 1500 bp in the L7 promoter sequence (SEQ ID NO: 1), particularly, any fragment of consecutive 1006 to 1319 bp in the L7-3 promoter sequence (SEQ ID NO: 3) containing the L7-4 promoter sequence shown in SEQ ID NO: 4, can be utilized as the modified L7 promoter of the present invention as long as it contains at least the L7-4 promoter sequence shown in SEQ ID NO: 4.

In the present specification, the "stringent conditions" can be achieved by conditions which involve: overnight incubation at 55° C. with a nucleic acid consisting of the nucleotide sequence shown in SEQ ID NO: 1 in a solution containing 6×SSC (1×SSC composition: 0.15 M NaCl, 0.015 M sodium citrate, pH 7.0), 0.5% SDS, 5×Denhardt's solution, 100 µg/ml denatured fragmented salmon sperm DNA, and 50% formamide; and washing under conditions such as low ionic strength, for example, 2×SSC, in a more stringent condition, 0.1×SSC and/or a higher temperature, for example, 37° C. or higher, in a stringent condition, 42° C. or higher, in a more stringent condition, 50° C. or higher, in a much more stringent condition, 60° C. or higher.

3. Preparation of Purkinje Cell-Tropic Vector

The vector of the present invention is prepared, for example, by: operably linking a therapeutic gene to a viral vector plasmid; transfecting an appropriate host cell with the vector plasmid; and culturing the cell in a culture medium comprising a protease inhibitor to produce a virus.

As the "host cell," cells such as a HEK293FT cell and a HEK293T cell are usually used. The transfection with the vector plasmid is achieved by introducing all the plasmids constituting the vector system described in the preceding paragraph (packaging, envelope, and vector) to a host cell using a method known in the art such as a method using calcium ions [Cohen, S. N. et al.: Proc. Natl. Acad. Sci., USA, 69: 2110-2114 (1972)] or electroporation.

A culture medium known in the art such as MEM, α-MEM, D-MEM, BME, RPMI-1640, D-MEM/F-12, Ham's F-10, or Ham's F-12 can be selected appropriately depending on a cell to be cultured and can be used as a culture medium for virus culture.

The protease inhibitor added to the culture medium is not particularly limited. A protease inhibitor having a cathepsin K inhibitory activity can be used preferably. Commercially available cathepsin K inhibitors (e.g., Cathepsin K inhibitor I, Cathepsin K inhibitor II, and Cathepsin K inhibitor III (all manufactured by Merck Calbiochem)) as well as cathepsin inhibitors (e.g., Cathepsin inhibitor I, Cathepsin inhibitor II, and Cathepsin inhibitor III (all manufactured by Merck Calbiochem)) can be used as such a substance.

It is preferred that the culture medium is kept at pH 7.2 to pH 8.0 during virus generation. At pH lower than this range, the Purkinje cell tropism (selectivity) of the vector is reduced. At pH higher than this range, cell growth is deteriorated. With cell growth, the pH of the culture medium is sifted to the acidic zone. Therefore, in addition to the protease inhibitor, a reagent, such as HEPES, which has the effect of preventing pH reduction may be added appropriately to the culture medium.

In general, host cell culture is, but not limited to, performed under conditions involving 3 to 10% $CO_2$ and 30 to 40° C., particularly 5% $CO_2$ and 37° C. A culture time after transfection is not particularly limited and is on the order of at least 24 hours, 216 hours in longer case, preferably 36 to 72 hours, more preferably 40 to 48 hours.

When a lentiviral vector (trade name: pLenti6/V5-DEST) manufactured by Invitrogen is used without any modification, a high titer can not be achieved. However, a high titer ($10^7$ TU/ml) can be achieved by removing an SV40 promoter and a blasticidin resistance gene from the vector (see Japanese Patent Application No. 2005-231514).

4. Gene Therapy Using Purkinje Cell-Tropic Vector

The vector of the present invention is useful as a delivery vector to Purkinje cells in gene therapies, because it has exceedingly high affinity and selectivity for Purkinje cells. Specifically, the vector of the present invention is useful as a pharmaceutical composition for the treatment of "Purkinje cell-affecting disease" caused by the damage of Purkinje cells. The pharmaceutical composition is prepared by dissolving/suspending the vector of the present invention, together with a pharmacologically acceptable carrier, in an appropriate buffer and injected to the cerebellar cortex and/or a subarachnoid space on the surface of the cerebellum.

Examples of the "Purkinje cell-affecting disease" can include polyglutamine disease including spinocerebellar ataxia and Huntington disease, Niemann-Pick disease, ataxia-telangiectasia, autism, Alzheimer's disease, fetal alcohol syndrome (FAS), alcoholism, and age-related cerebellar ataxia.

The "therapeutic gene" linked to the vector of the present invention is a gene that is useful in the treatment of the Purkinje cell-affecting disease, when expressed in Purkinje cells. The therapeutic gene can be selected as follows depending on diseases to be treated by the gene.

For the purpose of treating the polyglutamine disease, genes encoding GTPase CRAG (Qin et al. J. cell Biol. 2006 Feb. 13; 172 (4): 497-504), ubiquitin chain assembly factor E4B (UFD2a) (Matsumoto et al. EMBO J. 2004 Feb. 11; 23 (3): 659-69), ATPase VCP/p97 (Hirabayashi et al. Cell Death Differ. 2001 October; 8 (10): 977-84), molecular chaperons HDJ-2 HSDJ (Cummings et al. Nat. Genet. 1998 June; 19 (2): 148-54) and BiP (Kozutsumi et al. Nature. 1988 Mar. 31; 332 (6163): 462-4), a endoplasmic reticulum protein degradation-promoting molecule, i.e., ER degradation enhancing alpha-mannosidase-like protein (EDEM) (Oda et al. Science. 2003 Feb. 28; 299 (5611): 1394-7), and ER sensor molecules (Endoplasmic reticulum (ER) stress transducers), i.e., CREB/ATF family members OASIS (Kondo et al. Nat Cell Biol. 2005 February; 7 (2): 186-94), IRE1 (Welihinda and Kaufman. J Biol. Chem. 1996 Jul. 26; 271 (30): 18181-7), PERK, and ATF6 (Yoshida et al. J Biol. Chem. 1998 Dec. 11; 273 (50): 33741-9), can be used.

Alternatively, for the purpose of treating spinocerebellar ataxia type 1, 2, or 6, siRNAs for genes encoding ataxin-1, ataxin-2, voltage-dependent calcium channel α1a subunit, and PKCγ genes can be used to suppress the expression of these genes. For the purpose of treating the Huntington disease, siRNA for huntingtin may be used to suppress the expression of the gene.

For the purpose of treating the Niemann-Pick disease, a gene encoding sphingomyelinase can be used as a therapeutic gene. For the purpose of treating the ataxia-telangiectasia, a gene encoding AT-mutated (atm) can be used as a therapeutic gene. For the purpose of treating the autism, genes encoding Reelin and Bcl-2 can be used as a therapeutic gene. For the purpose of treating the Alzheimer's disease, a gene encoding neprilysin can be used as a therapeutic gene. Furthermore, for the purpose of treating the fetal alcohol syndrome (FAS), the alcoholism, and the age-related cerebellar ataxia, genes encoding Bcl-2, DNF, and NGF can be used as a therapeutic gene.

The pharmacological evaluation of such gene therapies can be conducted, though differing depending on the type of disease to be treated, by: for the spinocerebellar ataxia, administering the vector to the cerebellar cortex and/or a subarachnoid space on the surface of the cerebellum and then conducting evaluation, cytologically, based on the prevention of denaturation and loss of cerebellar neurons including Purkinje cells, stellate cells, and basket cells and, clinically (or ethologically), based on the degree of improvement of cerebellar ataxia.

The pharmaceutical composition of the present invention is, preferably, administered by injecting it to a subarachnoid space on the surface of the cerebellum. The injected vector is not localized in Purkinje cells around the injection site, but can deliver the therapeutic gene with high affinity for the whole Purkinje cells and in a wide range. Moreover, the injection of the vector of the present invention to a subarachnoid space on the surface of the cerebellum is more convenient than injection to inferior olivary nuclei located in the deep region of the brain and to cerebellar nuclei previously reported using herpesviruses or adeno-associated viruses and can suppress the damage of the cerebral parenchyma. Therefore, this approach is excellent in clinical application.

For administration, it is preferred from the viewpoint of stably maintaining pressure in the brain during injection that means which permits injection at a constant speed, for example, a hamilton syringe, a micromanipulator equipped therewith, and a microinjection pump for injection, is used for mice. An injection speed and a dose are not particularly limited as long as pressure in the brain can be maintained at the speed and the dose. They may be set appropriately depending on the age and body weight of an individual, the severity of disease, and so on. For example, for mice, it is preferred that the pharmaceutical composition of the present invention is injected at a dose of 2 to 8 µl in total at a speed of 10 nl/min to 800 nl/min, preferably 50 nl/min to 400 nl/min, more preferably 100 nl/min to 200 nl/min.

The dose of the pharmaceutical composition of the present invention is not particularly limited as long as it is an amount suitable for exhibiting therapeutic effects. It may be set appropriately depending on the age and body weight of an individual, the severity of disease, and so on. Moreover, the number of doses of the therapeutic agent of the present invention may be any number sufficient for exhibiting therapeutic effects. When an adeno-associated virus, herpesvirus, Sendai virus, or lentivirus is used, a single dose may be enough because long-term gene expression has been confirmed. For increasing the copy number of gene incorporated and transforming a wider range of cells, the pharmaceutical composition of the present invention may be administered at approximately 3 doses by changing positions on the surface of the cerebellum while monitoring therapeutic effects.

5. Model Animal of Cerebellar Purkinje Cell-Affecting Disease

An expression of a particular gene can be suppressed or increased specifically for the Purkinje cells of a non-human mammal of interest by injecting the vector of the present invention to the subarachnoid space of the animal.

Examples of the non-human mammal that can be used can include, but not particularly limited to, mice, rats, rabbits, horses, sheep, dogs, cats, and monkeys. Particularly, from animals other than mice and rats, transgenic animals are difficult to produce. Therefore, the use of the vector of the present invention is very effective.

For example, the gene for cerebellar disease (genes with an abnormally expanded CAG repeat that encode ataxin-1, ataxin-2, ataxin-3, voltage-dependent calcium channel α1a subunit, or huntingtin, or a gene encoding PKCγ having a mutation (Klebe S. et al. New mutations in protein kinase Cgamma associated with spinocerebellar ataxia type 14. Ann Neurol. 2005 November; 58 (5): 720-9)) is introduced as a foreign gene into a non-human mammal using the vector of the present invention and expressed therein. As a result, the cerebellar Purkinje cell-affecting disease in which the gene is involved can be developed. Such a transgenic animal is useful as a model animal of cerebellar Purkinje cell-affecting disease or a model animal for studying the functions of the cerebellum.

6. Culture Medium and Kit for Preparing Purkinje Cell-Tropic Viral Vector

The present invention also provides a culture medium for preparing a Purkinje cell-tropic viral vector comprising a substance having a cathepsin K inhibitory activity and a kit for preparing a Purkinje cell-tropic viral vector comprising, as a component, such a culture medium (a substance having a cathepsin K inhibitory activity and a cell culture medium, or a cell culture medium comprising a substance having a cathepsin K inhibitory activity).

The culture medium of the present invention is prepared by adding a substance having a cathepsin K inhibitory activity to a culture medium known in the art such as MEM, α-MEM, D-MEM, BME, RPMI-1640, D-MEM/F-12, Ham's F-10, or Ham's F-12. Cathepsin K inhibitors (e.g., Cathepsin K inhibitor I, Cathepsin K inhibitor II, and Cathepsin K inhibitor III (all manufactured by Merck Calbiochem)) as well as cathepsin inhibitors (e.g., Cathepsin inhibitor I, Cathepsin inhibitor II, and Cathepsin inhibitor III (all manufactured by Merck Calbiochem)) can be used appropriately as the substance having a cathepsin K inhibitory activity. However, the present invention is not limited to them.

The culture medium may appropriately contain a reagent, such as HEPES, which has the effect of preventing pH reduction such that the culture medium is kept at pH 7.2 to pH 8.0 during virus generation.

The kit of the present invention may contain, in addition to the essential component(s) (a substance having a cathepsin K inhibitory activity and a cell culture medium, or a cell culture medium comprising a substance having a cathepsin K inhibitory activity), a calcium chloride solution or Hank's balanced salt solution (HBSS) for viral plasmid transfection, a phosphate buffer, and a filter (of, e.g., 0.22 µm in pore size) for filtration sterilization. The calcium chloride is prepared, for example, by adding 36.76 g of $CaCl_2 2H_2O$ to 100 ml of purified water, followed by filtration sterilization. Moreover, the Hank's balanced salt solution (2×HBSS) is prepared, for example, by mixing 8.2 g of NaCl (final 0.28 M), 5.95 g of HEPES (final 0.05 M), 0.108 g of $Na_2HPO_4$ (final 1.5 mM), and 400 ml of $H_2O$, adjusting the pH to 7.05 with 5 N NaOH, and adding purified water to obtain the amount of 500 ml.

EXAMPLES

Hereinafter, the present invention will be described in more detail with reference to Examples. However, the present invention is not limited to these Examples.

Example 1

Influence of Culture Time after Transfection on Purkinje Cell Selectivity of Virus <Methods>
(1) Virus Generation The following procedures were performed in a P2 laboratory. HEK293FT cells were used in virus generation. As a culture medium, a conventional Dulbecco's modified Eagle's medium (D-MEM) supplemented with 10% bovine serum was used. HEK293FT cells in log phase growth were dispersed in a phosphate-buffered saline ($Mg^{2+}$- and $Ca^{2+}$-free) [PBS(−)] and subsequently plated onto a 10-cm dish (manufactured by Falcon) at a density of $5 \times 10^5$ cells per dish. To the 10-cm dish after plating, 10 ml of D-MEM containing 10% by weight of fetal bovine serum was added, and the cells were then cultured at 5% (by volume) $CO_2$ at 37° C. 24 hours later, the culture medium in the dish was replaced by 10 ml of a fresh culture medium (D-MEM containing 10% by weight of fetal bovine serum). Then, the cells were cultured at 5% (by volume) $CO_2$ at 37° C. for 0.5 hours.

The following plasmids: 6 μg of pCAGkGP1R (St. Jude Children's Research Hospital), 2 μg of pCAG4RTR2 (St. Jude Children's Research Hospital), 2 μg of pCAG-VSV-G (St. Jude Children's Research Hospital), and 10 μg of pCL20c MSCV-GFP (St. Jude Children's Research Hospital/George Washington University) were separately dissolved in 450 μl of sterilized water to obtain plasmid solutions.

pCAGkGP1R: a packaging plasmid containing gag (encoding viral structural proteins) and pol (encoding reverse transcriptase).

pCAG4RTR2: a plasmid containing tat (transcriptional control gene). The virion cannot replicate in hosts due to the deletion of rev.

pCAG-VSV-G: VSV-G is an abbreviation of a vesicular stomatitis virus glycoprotein. A lentivirus having the original envelope can infect only CD4-positive cells. The original envelope was substituted by an envelope of VSV (vesicular stomatitis virus) which is targeting to phospholipid to obtain the envelope plasmid which causes infection to various cells including neurons.

pCL20c MSCV-GFP: a plasmid which was constructed by locating an MSCV promoter located into two LTRs in a main vector pCL20c of a lentivirus and linking a GFP gene thereto (FIG. 1).

As described above, genes essential for virus generation were divided to four plasmids, and regions such as regions necessary for replication were deleted. A virus so generated has an infectious ability but has higher safety because of a lack of a self-propagating ability after infection.

To the obtained plasmid solutions, 50 μl of 2.5 M $CaCl_2$ was added, and the mixture was stirred. 500 μl of 2×HBSS [composition: 50 mM HEPES, 0 mM NaCl, 1.5 mM $Na_2HPO_4$, pH 7.05] was added to the mixture, and stirred immediately.

The plasmid solutions were aliquoted dropwise to the dish and gently mixed with the medium in the dish. Then, the cells were cultured at 5% (by volume) $CO_2$ at 35° C. Subsequent procedures were performed in a biological safety cabinet.

16 hours later, the medium in the dish was replaced by 10 ml of a fresh medium (D-MEM containing 10% by weight of fetal bovine serum). The cells were further cultured at 5% (by volume) $CO_2$ at 37° C. The virus-containing culture medium was harvested 40 hours after transfection (40 h virus). Then, a fresh culture medium was added, and the cells were cultured for additional 24 hours. The virus-containing culture medium was harvested 64 hours after transfection (64 h virus) (see FIG. 2).

(2) Condensation

Each medium harvested in the paragraph (1) was transferred to a 50-ml centrifuge and centrifuged at 1000 rpm (120×g) for 4 minutes to obtain a supernatant. The obtained supernatant was filtered through a filter (Millipore, 0.22 μm in pose size). The obtained filtrate was subjected to ultracentrifugation (25,000 rpm, 2 hours, 4° C.) using a rotor SW28.1 manufactured by Beckman Coulter to precipitate viral particles. The supernatant was removed.

The obtained viral particle pellets were suspended in PBS (−) to obtain a virus solution for infection in a final amount of 200 μl. The virus solution which was not immediately used was dispensed in 20 μl aliquots and stored at −80° C.

(3) Titration of Virus (i) Method Based on GFP Fluorescence

HeLa cells in log phase growth were dispersed in PBS(−) and subsequently plated onto a 12-well dish (manufactured by Iwaki Glass) at a density of $5 \times 10^4$ cells per well. To the 12-well dish after plating, D-MEM containing 10% by weight of fetal bovine serum was added at a concentration of 1 ml/well, and the cells were then cultured at 5% (by volume) $CO_2$ at 37° C. for 24 hours.

The virus solution was added to the medium in the wells to be $10^3$ to $10^5$ times dilution. Simultaneously, Hexadimethrine Bromide (SIGMA, trade name: Polybrene) was added at a concentration of 6 μg/ml to each well. Then, the cells were cultured at 5% (by volume) $CO_2$ at 37° C. for 88 hours.

Green fluorescent protein (GFP)-expressing cells in the wells were counted using a cell counter (As One Corp., trade name: Counter) under a fluorescence microscope (Olympus Corp., trade name: CKX41) to determine a virus titer. When the addition of a $10^X$ diluted virus solution resulted in Y cells expressing GFP, the virus titer is calculated as $Y \times 10^X$ TU/ml (TU: transduction unit).

(ii) Evaluation Based on the Copy Number of Provirus Incorporated into Genomes of Cultured Cells (HeLa cells) (Izopet et al. J Med. Virol. 1998 January; 54 (1): 54-9.)

HeLa cells were cultured in 10-cm dishes and infected with the virus solution 24 hours after plating. 3 days after the infection, $5.0 \times 10^6$ cells were harvested. In parallel with this, the equivalent number of LAV-8E5 cells (ATCC, Manassas, Va., USA) were prepared. The LAV-8E5 cells, which have 1 copy of HIV type 1 provirus per cell, were used as a standard. Genomic DNA was extracted from these cells and finally suspended in 100 μl of TE buffer. A 290-bp region contained in RRE (rev responsive element) of the HIV provirus was amplified using 1 μl aliquot of the genomic DNA solution and the following primers:

```
5'-ATGAGGGACAATTGGAGAAGTGAATTA-3'    (SEQ ID NO: 9)
and

5'-CAGACTGTGAGTTGCAACAGATGCTGT-3'.   (SEQ ID NO: 10)
```

The copy number of provirus incorporated into the genome was determined by limiting dilution of the genomic DNA. Specifically, a dilution ratio was determined immediately before no bands were observed, and compared with the standard using the LAV-8E5 cells to calculate the copy number of provirus incorporated per $5.0 \times 10^6$ HeLa cells (the genomic copy number/ml virus solution).

(4) Injection of Vector to Subarachnoid Space in Mouse Cerebellum

Mice (supplied from SLC, 4 to 10 weeks old) were anesthetized by intraperitoneal administration (40 mg/kg body weight) of pentobarbital (trade name: Nembutal). The following procedures were performed in a biological safety cabinet.

After anesthesia, the mice were fixed using a small animal stereotaxic apparatus (manufactured by NARISHIGE, trade name: SG-4). Moreover, the body temperatures of the mice were kept at 37° C. using a body temperature controller (manufactured by FST, trade name: Body Temperature Control System (for mice) FST-HPSM). Hair on the mouse heads was clipped. Then, the skin was incised from a few millimeters rostral to bregma to directly above the cerebellum. Subsequently, a hole of 2 to 3 mm in interior diameter was made in the skull at the midline 5 to 7 mm caudal to bregma using a microdrill (Urawa Corp., trade name: Power Controller UC100+HB1 (drill)) under a stereoscopic microscope (Nikon Corp., trade name: 1SMZ645). Moreover, a hole was made in the dura mater and arachnoid mater beneath the bone using an injection needle.

The obtained lentiviral vector was charged to a Flexifil microsyringe (trade name, manufactured by WPI, 10 μl volume), and the Flexifil microsyringe was set in Ultramicropump 2 (manufactured by WPI) attached to a micromanipulator.

The needle tip of the microsyringe was inserted approximately 0.5 mm through the hole in the dura mater made directly above the cerebellum and placed in the subarachnoid space. Then, the lentiviral vector was injected at a dose of 4 μl in total at a speed of 100 nl/minute for 40 minutes using an Ultramicropump 2-specific digital controller Micro 4 (trade name, manufactured by WPI).

After injection, the incised mouse skin was sutured with an opthalmological microneedle with threads (manufactured by Natsume Seisakusho Co., Ltd., trade name: Opthalmological Slightly Curved Needle C67-0). Then, the mice were removed from the stereotaxic apparatus and observed in a cage (in the safety cabinet) placed on a heating pad (Showa Mold & Engineering Co., Ltd., trade name: Rubber Mat Heater SG-15). The mice were awakened from anesthesia and then raised in the mouse cage placed in a rack with an HEPA filter for infected animals (Tokiwa Kagaku Kikai Co., Ltd., trade name: Bio Clean Capsule Unit T-BCC-M4).

7 days after injection, the mice were subjected to perfusion fixation with 4% formaldehyde-phosphate buffer, and the brains were excised. Images of the whole brains and fluorescence images of GFP were taken using a fluorescence stereoscopic microscope. Then, sagittal sections of the cerebellums of 50 μm or 100 μm in thickness were prepared using a microslicer (Dosaka EM, trade name: DTK-1000). The prepared brain sections were incubated at room temperature for 24 hours with a primary antibody [mouse monoclonal anti-parvalbumin (marker for stellate cells and basket cells) manufactured by SIGMA, mouse monoclonal anti-GFAP (marker for glial cells) manufactured by Chemicon, mouse monoclonal anti-neuron-specific nuclear protein (NeuN, marker for granule cells) manufactured by Chemicon, or mouse monoclonal anti-mGluR2 (marker for Golgi cells) donated from Professor R. Shigemoto, National Institute for Physiological Sciences] and subsequently incubated at room temperature for 2 hours with a secondary antibody (Alexa Fluor 568-conjugated anti-mouse IgG manufactured by Invitrogen) to obtain samples for microscopic examination. Then, the localization of GFP proteins expressed and the types of GFP-expressing cells were examined by observing the samples using a fluorescence microscope (Leica, trade name: DMI 6000B) and a confocal microscope (CarlZeiss, trade name: LSM5 Pascal).

<Results>

Figure 2:
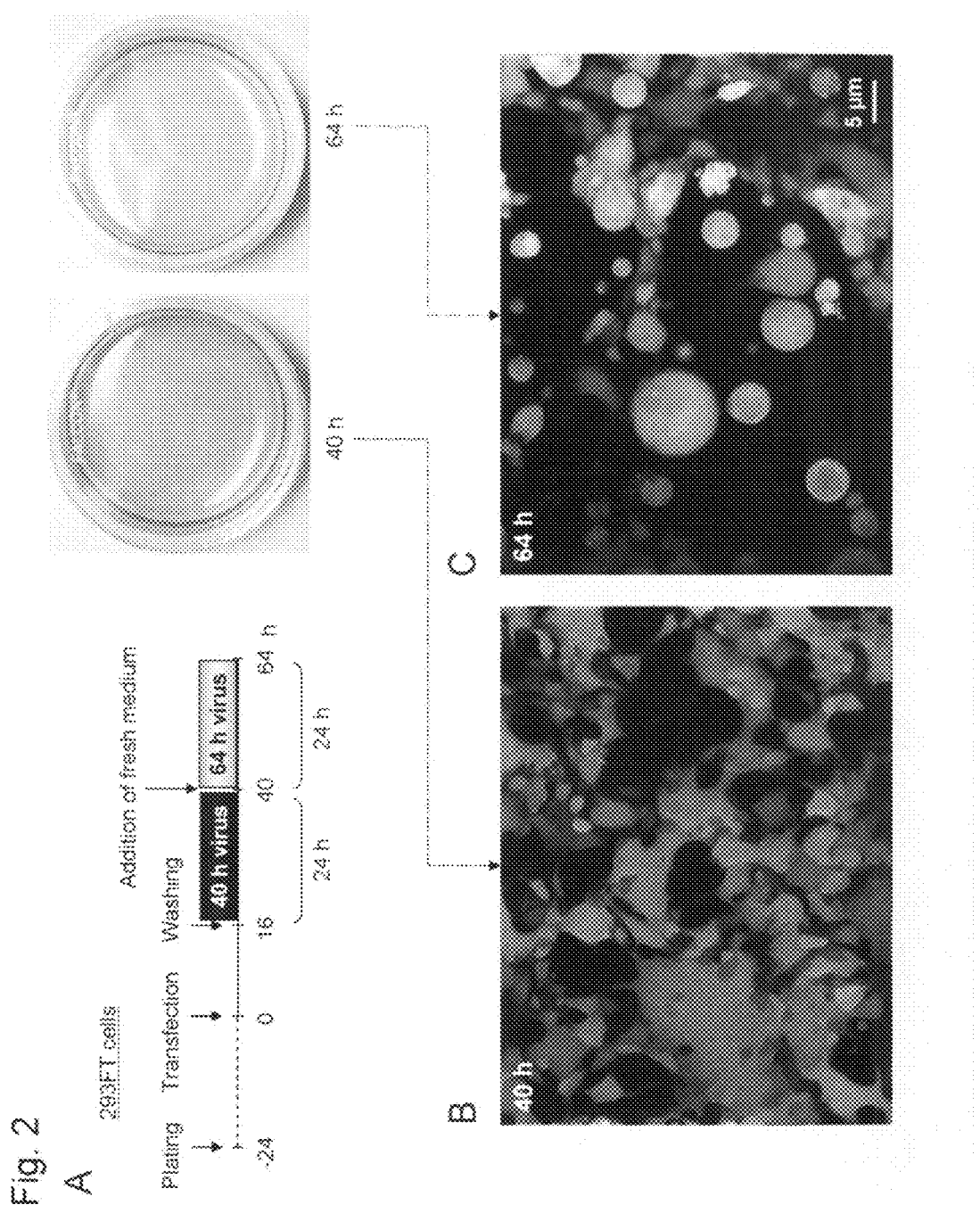
FIG. 2A shows experimental procedures of Example 1.
FIG. 2B shows GFP expression in HEK293FT cells immediately before harvest of a virus 40 hours after transfection.
FIG. 2C is a fluorescence microscope image showing GFP expression in HEK293FT cells immediately before harvest of a virus 64 hours after transfection.
Figure 3:
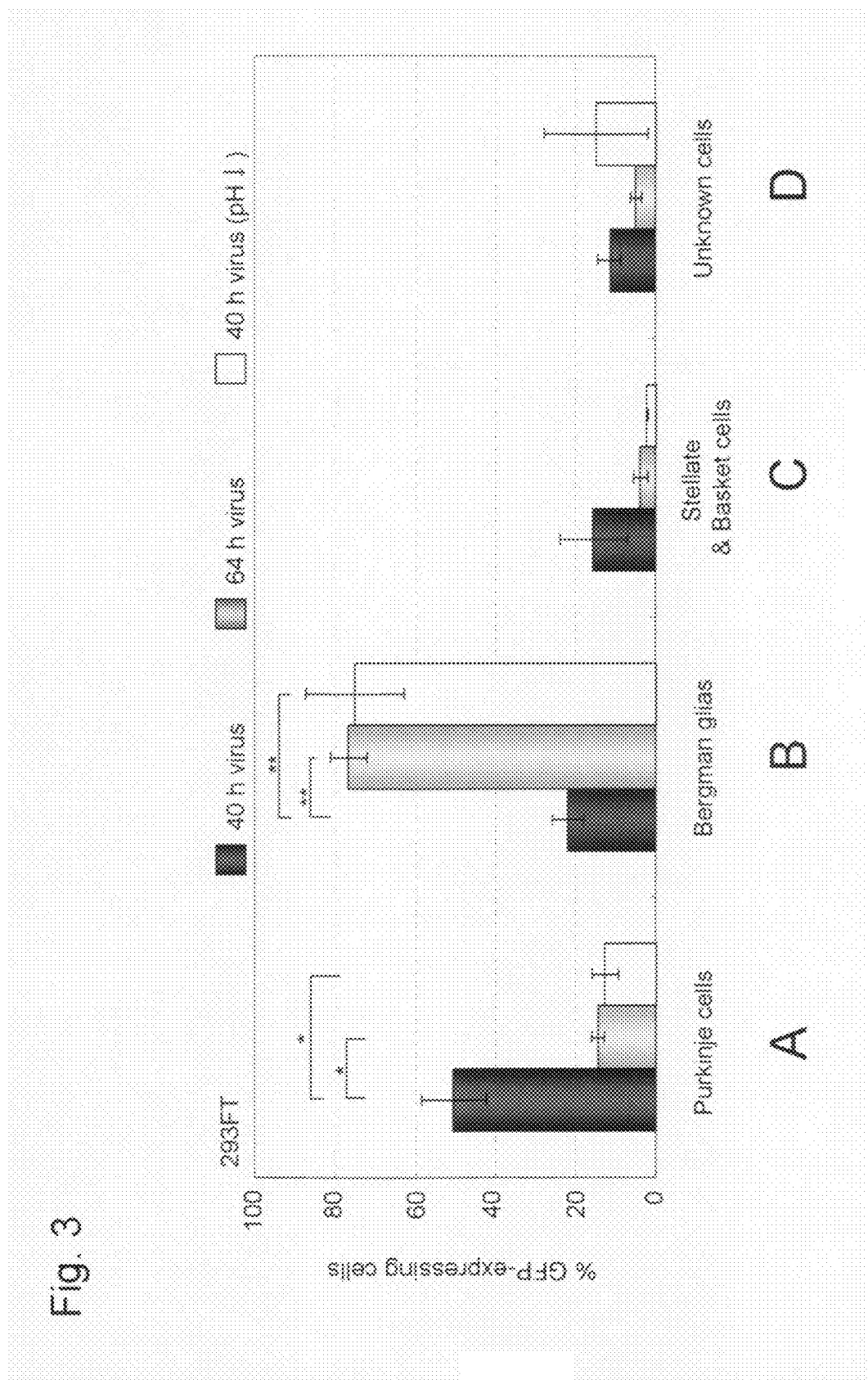
FIG. 3 is a graph showing the proportion (%) of each GFP-expressing cell to all GFP-expressing cells in the cerebellar cortex 1 week after injection of a virus harvested 40 hours after transfection (left bar), a virus harvested 64 hours after transfection (center bar), or a virus harvested after adjustment of pH of a culture medium containing a virus 40 hours after transfection to 7.0 by the addition of diluted hydrochloric acid (right bar). (A shows Purkinje cells, B shows Bergmann glia, C shows stellate & basket cells, and D shows unknown cells.

Purkinje cells occupied approximately a half (51%) of all GFP-expressing cells obtained by the inoculation of a virus released into the culture medium 40 hours after transfection. This was followed by Bergmann glia (22%) and stellate cells/basket cells (16%) (FIGS. 2 and 3). On the other hand, the proportions of GFP-expressing cells obtained by the inoculation of a virus released into the culture medium from 40 hours to 64 hours after transfection (64 h virus) were lower for Purkinje cells (15%) and stellate cells/basket cells (4%) and higher for Bergmann glia (77%) (FIGS. 2 and 3).

As shown in Table 1, the pH of the culture medium is 7.2 (40 hours after transfection) and is reduced to 7.0 (64 hours after transfection). Thus, it appears that reduction in affinity for Purkinje cells is attributed to changes in culture medium pH.

TABLE 1 pHs of virus-containing medium samples and titers of virus stocks

| Host cell | Culture period$^a$ | pH$^b$ | Biological titer (TU/ml) | n$^d$ |
|---|---|---|---|---|
| HEK 293FT | 40 h | 7.2 | $5.1 \pm 2.6 \times 10^8$ | 4 |
| | 64 h | 7.0 | $4.4 \pm 2.1 \times 10^8$ | 4 |
| | 40 h | 7.0$^c$ | $2.5 \pm 2.1 \times 10^8$ | 3 |

$^a$Time (h) after transfection.
$^b$pH of conditioned medium at harvest.
$^c$pH of conditioned medium was adjusted to 7.0 by HCl.
$^d$Number of cultures that were independently conducted.

Example 2

Influence of Culture Medium pH During Virus Generation on Purkinje Cell Selectivity Based on the results of Example 1, the relationship between culture medium pH and Purkinje cell selectivity was studied.

<Methods>

According to Example 1, the pH of the culture medium containing a virus 40 hours after transfection was adjusted to 7.0 by the addition of diluted hydrochloric acid. Then, the virus was similarly purified and injected to the mouse cerebellums. 7 days later, brain sections were observed. Furthermore, a similar experiment was conducted using HEK293T cells which proliferate more slowly than HEK293FT cells and thus delay the acidification of the culture medium attributed to proliferation.

<Results>

The pH (7.2) of the culture medium 40 hours after transfection was shifted by 0.2 to the acidic zone (pH 7.0). The virus was similarly injected to the mouse cerebellums. As expected, almost the same results as those provided by harvest 64 hours after transfection were obtained. Specifically, GFP-expressing cells were Purkinje cells (14%), Bergmann glia (72%) and stellate cells/basket cells (1.7%) (FIG. 3, 40 h virus (pHs1) and FIG. 4). When HEK293T cells which grow more slowly than HEK293FT cells are used, they delay the acidification of the culture medium. In this case, it was demonstrated that a virus having high affinity for Purkinje cells is obtained even if the virus is generated in the same way. This indicates that selectivity for Purkinje cells is largely influenced by culture medium pH during virus generation even if a VSV-G envelope having the ability to bind to phospholipid (phosphatidylserine) serving as a component of cell membranes is used.

Example 4

Influence of Protease Inhibitor on Purkinje Cell Selectivity

<Methods>

In the presence of various kinds of protease inhibitors shown in Table 3 instead of serum, viruses were generated in HEK293T cells according to the procedures of Example 1. The Purkinje cell selectivity of gene expression by the purified viruses in the mouse cerebellums was studied.

TABLE 3

|  |  | Conc. | n (Culture) | Titer × $10^9$ | n (Mice) |
|---|---|---|---|---|---|
| Serum free | Serum-free | — | 5 | 7.0 ± 1.5 | 7 |
|  | Serum-free(+ Insulin, Transferrin, Selene) | — | 4 | 3.6 ± 1.3 | 5 |
| Serum(+) | Biological Industries Israel (Lot No. 716543) 40 h pH 7.2 | 10% | 4 | 2.6 ± 0.4 | 5 |
|  | Biological Industries Israel (Lot No. 716543) 64 h pH 7.0 | 10% | 4 | 2.4 ± 0.5 | 6 |
|  | Biological Industries Israel (Lot No. 716543) 40 h PH 7.0 | 10% | 3 | 3.4 ± 1.2 | 5 |
|  | HyClone Laboratories, Inc. 0 USA (Lot No. APA20504) | 10% | 3(2) | 2.1 ± 1.4 | 5 |
|  | HyClone Laboratories, Inc. 1 USA (Lot No. ANK19840) | 10% | 2 | ND | 2 |
|  | EQUITECH-BIO, Inc. USA (Lot No. SFB30-1540) | 10% | 4 | 6.9 ± 2.2 | 6 |
|  | GIBCO Mexico (Lot No. 1214677) | 10% | 3 | 6.4 ± 0.6 | 5 |
| Metallo proteinase inhibitor | CGS 27023A |  | 4 | 3.4 ± 1.4 | 5 |
|  | TIMP-1 |  | 1 | 6.3 | 1 |
| Serine & cysteine proteinase inhibitors | Proteinase inhibitor cocktail (EDTA free) (AEBSF, Aprotinin, E-64, Leupeptin) |  | 6 | 2.3 ± 0.7 | 7 |
| Cysteine proteinase inhibitor | Cathepsin inhibitor I |  | 5 | 8.3 ± 2.6 | 6 |
|  | Cathepsin K inhibitor |  | 6 | 4.8 ± 0.6 | 7 |
| Serine proteinase inhibitor |  |  |  |  |  |
| Aspartate proteinase inhibitor |  |  |  |  |  |

Example 3

Influence of Serum on Purkinje Cell Selectivity

<Methods>

Viruses were generated by the similar procedures as in Example 1 using 9 kinds of bovine sera differing in lot shown in Table 2 and studied for their respective selectivity for Purkinje cells.

TABLE 2

| Serum No. | Suppliers | Origin | LOT No. |
|---|---|---|---|
| S1 | GIBCO | USA | 1175763 |
| S2 | GIBCO | Mexico | 1214677 |
| S3 | EQUITECH-BIO, INC. | USA | SFB30-1540 |
| S4 | EQUITECH-BIO, INC. | USA | SFB30-1548 |
| S5 | Valley Biomedical | USA | J31041 |
| S6 | Biowest | Denmark | S04303S1750 |
| S7 | Biological Industries | Israel | 716543 |
| S8 | HyClone Laboratories | USA | APA20504 |
| S9 | HyClone Laboratories | USA | ANK19840 |
| S7-SF** | Biological Industries | Israel | 716543 |

SF; Serum free: HEK293T cells were transfected in the culture medium containing the serum S7. The serum was removed 24 h after the transfection.

<Results>

Figure 5:
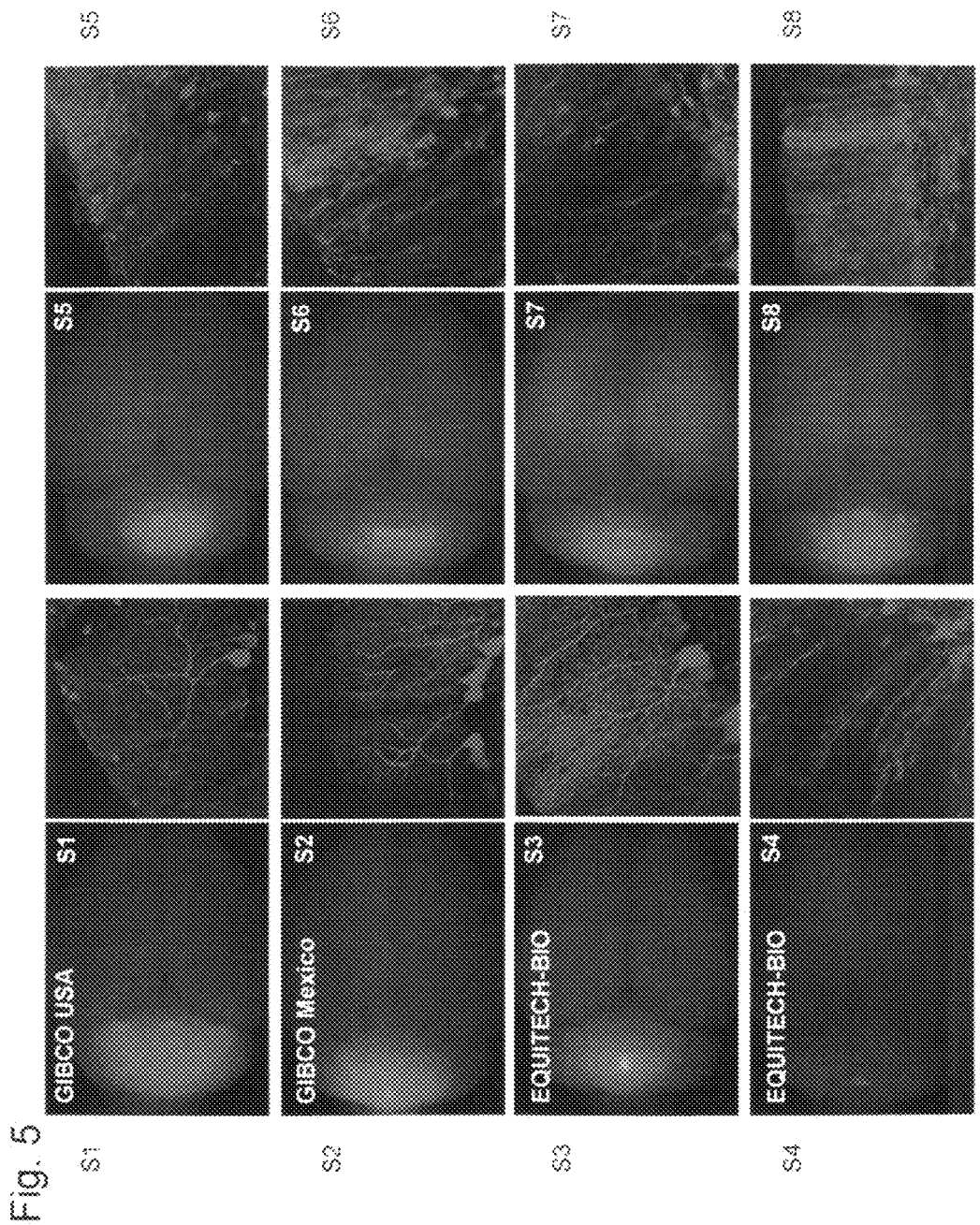
FIG. 5 is a fluorescence stereoscopic microscope photograph of the brain 1 week after injection, to the cerebellum, of a virus generated using 8 kinds of bovine sera differing in lot and then harvested and is a confocal scanning microscope image showing the appearance of GFP expression in a sagittal section thereof.

As shown in FIG. 5, it was shown that selectivity for Purkinje cells largely differs depending on a difference in serum lot. Furthermore, it was confirmed that viruses generated even under serum-free conditions, but have low selectivity for Purkinje cells and cause gene expression in various cells.

All the titers of the viruses were adjusted to $1 \times 10^9$ TU/ml. Then, the viruses were injected to the mouse cerebellums. 1 week later, sagittal slices of the cerebellums of 100 μm in thickness were prepared. Serial confocal images at 2-μm intervals of optical sectioning from the bottom to the top of the slice were obtained (20× objective lens) and GFP signals were reconstructed three-dimensionally. Evaluation was conducted by the following two methods:

(1) the ratio (%) of GFP-expressing Purkinje cells to all GFP-expressing cells was determined in a visual field (0.95 mm$^2$). This represents the selectivity of viral infections for Purkinje cells; and (2) the ratio (%) of GFP-expressing Purkinje cells to all Purkinje cells was determined in the visual field. This represents the efficiency of viral infections of Purkinje cells.

<Results>

Figure 6:
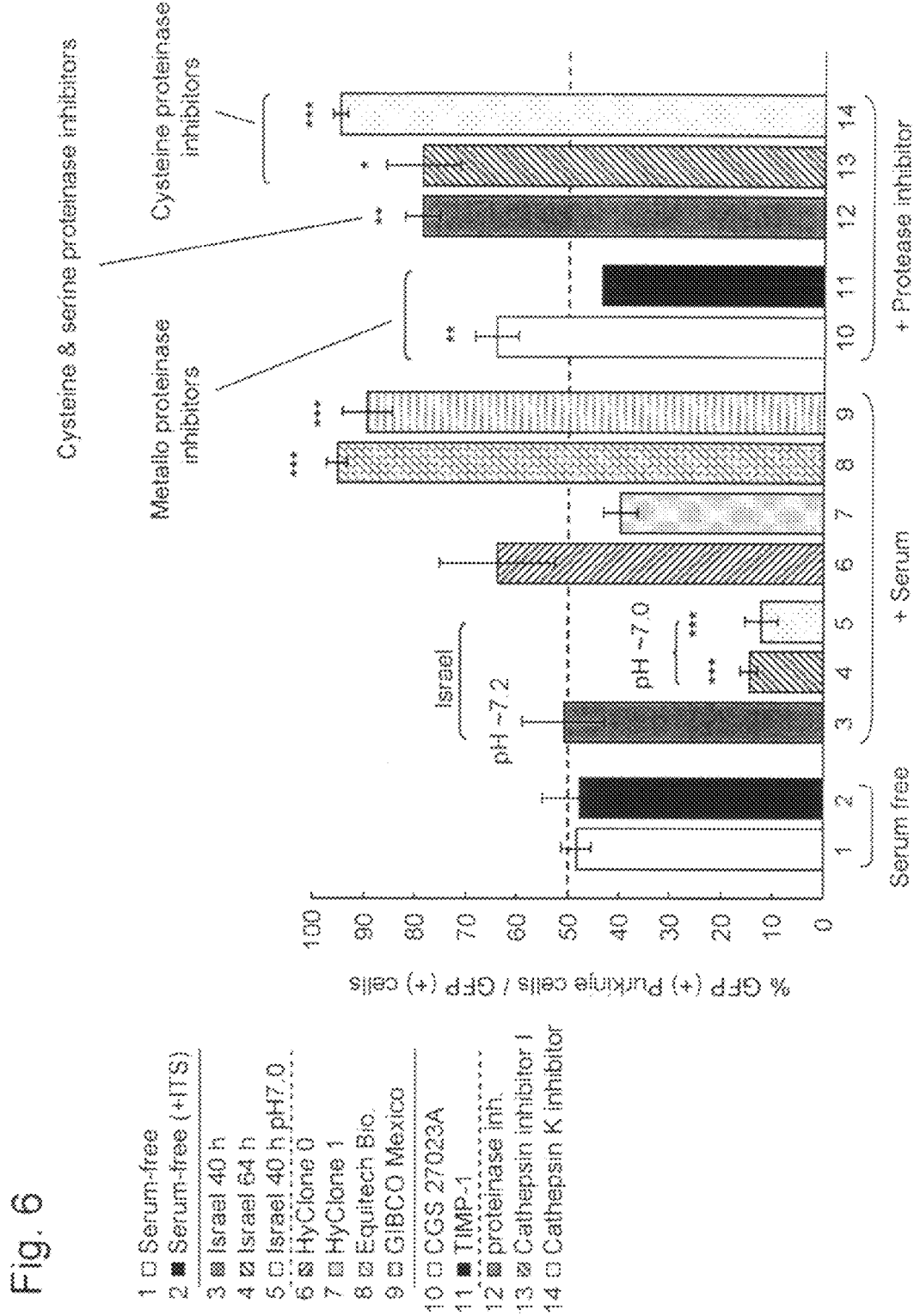
FIG. 6 is a graph showing the proportion (%) of GFP-expressing Purkinje cells to all GFP-expressing cells in a visual field using a 20× objective lens.

(1) Selectivity for Purkinje Cells (FIG. 6)

A viral vector prepared in a medium containing D-MEM alone without the addition of serum and protease inhibitors had selectivity of 48% for Purkinje cells (Purkinje cells occupied approximately a half of GFP-expressing cells). Viruses generated in a medium supplemented with particular serum had larger selectivity (e.g., serum from Mexico manufactured by GIBCO) or had almost the same selectivity (serum manufactured by HyClone Laboratories, Inc.). By contrast, viruses generated in a medium supplemented with a protease inhibitor without the addition of serum had much larger Purkinje cell selectivity for all the inhibitors used except for TIMP-1. Particularly, Purkinje cell selectivity was significantly increased by the addition of the cathepsin K inhibitor.

Figure 7:
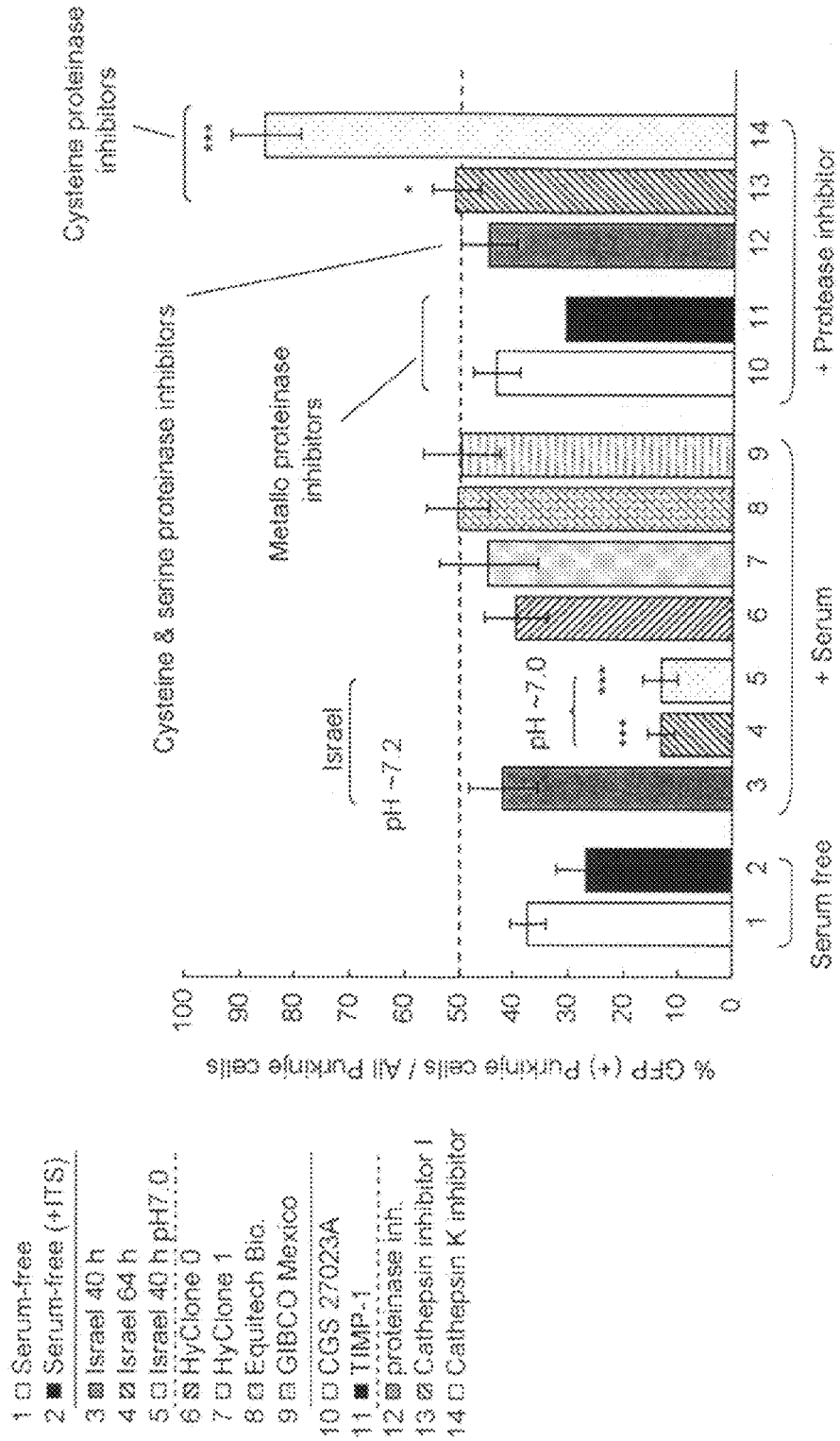
FIG. 7 is a graph showing the proportion (%) of GFP-expressing Purkinje cells to all Purkinje cells in a visual field using a 20× objective lens.

(2) Gene Expression Efficiency in Purkinje Cells (FIG. 7)

A viral vector prepared in a medium containing D-MEM alone without the addition of serum and protease inhibitors had gene expression efficiency of 37% in Purkinje cells (37% of all Purkinje cells in the visual field expressed GFP genes). Unlike the results of selectivity, no significant increases in gene expression efficiency in Purkinje cells were observed even though serum lot used was changed. Likewise, no significant increases in gene expression efficiency in Purkinje cells were observed even by the addition of 3 out of 5 kinds of protease inhibitors. However, gene expression efficiency in Purkinje cells was observed to be much higher (86%) by the addition of cathepsin K inhibitor.

From these results, it was deduced that when a lentiviral vector is prepared by conventional protocols involving the addition of serum, the selectivity of the viral vector for Purkinje cells and gene expression efficiency are influenced by the functions of protease in a medium. Particularly, cathepsin K, a member of cysteine protease family, presumably plays a large role in this phenomenon. It was shown that a virus having very high selectivity and high affinity for Purkinje cells can be generated by adding a cathepsin K inhibitor to a medium during virus generation.

Example 5

Influence of Cathepsin K Inhibitor on Purkinje Cell Selectivity and Viral VSV-G

1. Culture Medium pH and Cathepsin K Activity in Culture Medium

<Methods>

A culture medium (pH 7.2) 40 hours after transfection and a culture medium (pH 7.0) 64 hours after transfection are obtained by the procedures of Example 1. A cathepsin K activity in these two culture media is measured using Cathepsin K Detection Kit (Merck Calbiochem).

2. Cleavage of VSV-G with Cathepsin K

<Methods>

40 h and 64 h viruses are produced and harvested. Moreover, the culture medium 40 hours after transfection is treated with cathepsin K. Alternatively, its pH is decreased to 7.0 using diluted hydrochloric acid. Then, the virus is harvested. In these 4 kinds of viruses, the state of cleavage of VSV-G proteins is examined by direct amino-terminal sequencing to confirm a site where the cleavage has occurred.

3. Purkinje Cell Selectivity is Reduced by Treatment of Virus with Cathepsin K

<Methods>

A culture medium containing viral particles is obtained 40 hours after transfection according to the procedures of Example 1. This culture medium is treated with cathepsin K for 2 hours. Then, the virus is harvested by ultracentrifugation and injected to the mouse cerebellums. 1 week later, it is confirmed that the Purkinje cell selectivity of the virus is reduced. Cathepsin K mRNA has been previously extracted from HEK293T cells, and its gene has been obtained using an RT-PCR method (the acquirement of the cathepsin K gene from HEK293T cells by RT-PCR indicates that the HEK293T cells express cathepsin K). The cathepsin K gene is further subcloned into a pcDNA3.1 vector, and this vector is transfected into HEK293T cells. 3 days later, the culture medium is collected. It is also confirmed by a western blot method using a rabbit polyclonal anti-cathepsin K antibody (manufactured by BioVision) that this culture medium contains a sufficient amount of cathepsin K. The virus is treated with the cathepsin K thus obtained.

Example 6

Preparation of Disease Model Mice Using Causative Gene of Purkinje Cell Damage

<Methods>

A causative gene of spinocerebellar ataxia type 3 (MJD: Machado-Joseph disease) is ataxin-3. In patients with this disease, a CAG repeat present in this gene is abnormally expanded. Thus, ataxin-3 gene having an abnormally expanded CAG repeat was expressed in Purkinje cells using a lentiviral vector to prepare model mice for MJD.

<Results>

Figure 8:
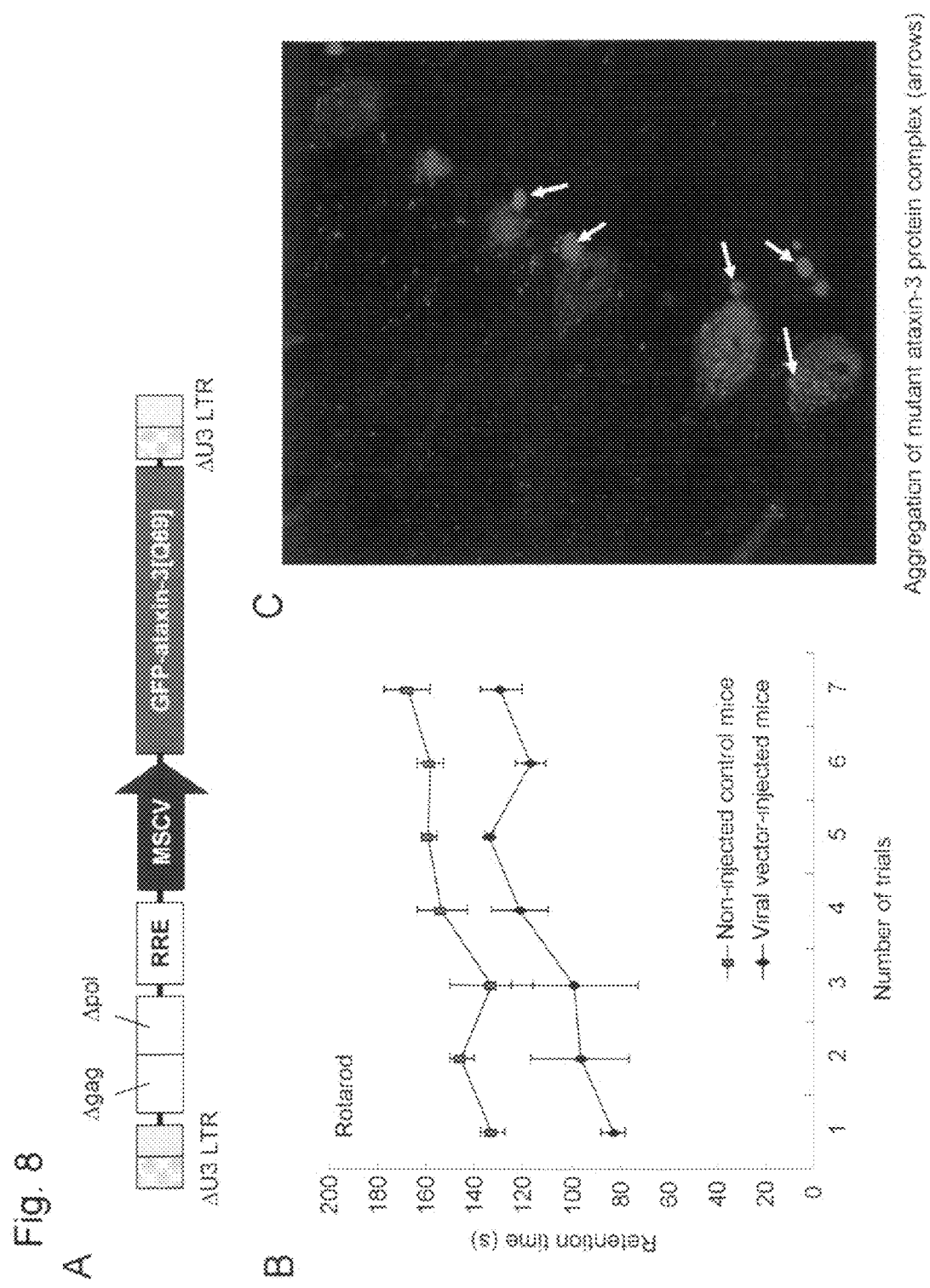
FIG. 8A is a schematic diagram showing the structure of a proviral portion of a virus expressing a spinocerebellar ataxia type 3 gene ataxin-3 [Q69] fused with a GFP gene.
FIG. 8B shows results of a rotarod test conducted 2 months after injection of this virus to the cerebellum.
FIG. 8C shows GFP-fused ataxin-3 [Q69] aggregates in the Purkinje cells of this mouse.

A vector plasmid was prepared such that ataxin-3 having an abnormally expanded CAG repeat was expressed under the control of an MSCV promoter (FIG. 8A). Next, a 40 h virus was prepared according to the procedures of Example 1. HEK293T cells were used as host cells for virus generation. The obtained virus was injected to the mouse cerebellums. 2 months later, the severity of cerebellar ataxia was analyzed using a rotarod (Muromachi Kikai Co., Ltd., MK-660C). The rod was adjusted such that it initially stood still and was gradually accelerated to a speed of 40 rpm after 180 seconds. The retention time when the mouse was placed on the rod was measured. The experiment was repeated 8 times. Mice expressing GFP in their cerebellums by the virus have been previously confirmed to have no difference in rotarod test results from non-injected control mice. By contrast, the virus-injected mice fell off the rod in a significantly shorter time than non-injected control mice, showing that ataxia appeared (FIG. 8B). After the completion of the experiments, the mice were subjected to perfusion fixation, and their cerebellar slices were prepared and observed. As a result, ataxin-3 aggregates were observed in Purkinje cells (arrows in FIG. 8C).

Thus, it was shown that cerebellar disease model mice can be prepared by expressing a causative disease of the cerebellar disease by Purkinje cells using a virus.

Example 7

Study on Therapeutic Effects of Therapeutic Gene-Expressing Virus Using Spinocerebellar Ataxia Model Mice <Methods>

A DNA construct (FIG. 9A) was prepared such that a spinocerebellar ataxia type 3 gene ataxin-3 [Q69] having an abnormally expanded CAG repeat was expressed under the control of a Purkinje cell-specific L7 promoter. This construct was injected to mouse fertilized eggs and transgenic mice (spinocerebellar ataxia model mice) of 3 lines highly expressing ataxin-3 [Q69] specifically in cerebellar Purkinje cells were produced. A viral vector expressing CRAG which is a therapeutic gene candidate or VCP in which cysteine at position 522 of VCP/p97 had been substituted by threonine (C522T) (FIG. 10A) was injected to the cerebellums of these mice, and whether or not they rescued from ataxia was observed (FIGS. 10B to 10E).

<Results>

Figure 9:
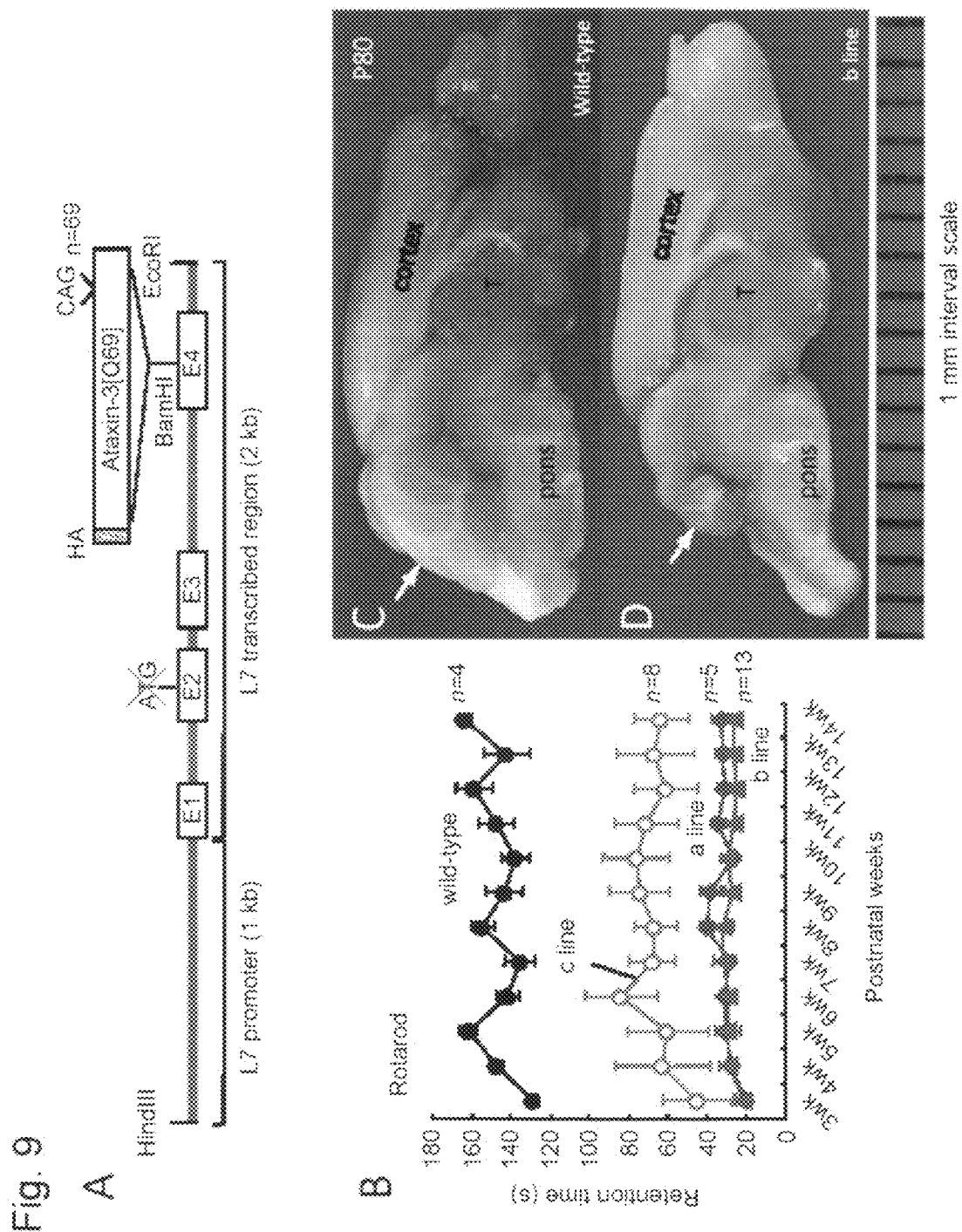
FIG. 9A is a schematic diagram of a construct used in the production of mice expressing a spinocerebellar ataxia type 3 gene ataxin-3 [Q69] under the control of a Purkinje cell-specific L7 promoter.
FIG. 9B shows results of a rotarod test from postnatal 3 weeks through 14 weeks of spinocerebellar ataxia type 3 model mice of 3 lines (a, b, and c lines) produced.
FIG. 9C shows a sagittal section through the brain of a postnatal 80-day-old wild-type mouse.
FIG. 9D shows a sagittal section through the brain of the spinocerebellar ataxia type 3 model mouse of the b line of the same age.

Of the produced spinocerebellar ataxia model mice of 3 lines, the a and b lines exhibited exceedingly strong ataxia immediately after birth (FIG. 9B) and had distinct cerebellar atrophy (FIGS. 9C and 9D). By contrast, the c line was intermediate in the severity of ataxia when compared to wild-type mice and the a and b lines (FIG. 9B). A CRAG expressing virus was injected to the cerebellums of the postnatal 30-day-old model mice of the c line, and a rotarod test (the rod initially stood still and was accelerated to a speed of 40 rpm in 180 seconds) was conducted at 1-week intervals. 1 week after injection, the injected model mice were observed to have almost no difference from non-injected model mice. However, the virus-injected mice were then gradually improved in results (FIG. 10C). Specifically, the spinocerebellar ataxia type 3 model mice remarkably rescued from ataxia by Purkinje cell-specific CRAG expression using the virus. A CRAG or GFP-expressing lentiviral vector was injected to the mice of the b line (postnatal 21 days old) with stronger ataxia. As a result, 4 weeks later, the model mice were observed to significantly rescue in rotarod test results (FIG. 10D). 8 weeks later, the model mice could stay on the accelerated rotarod for a further longer time (non-injected mice and GFP-expressing lentiviral vector-injected mice could stay only for a little less than 20 seconds, whereas the CRAG-expressing viral vector-injected mice could stay for 40 seconds or longer). 2 months after injection, 6 rotarod tests were conducted at a fixed speed of 5 rpm. As a result, non-injected mice and GFP-expressing lentiviral vector-injected mice fell off the rod immediately after the start of rotation in all trials. By contrast, the CRAG-expressing lentiviral vector-injected mice stayed on the rod for a time increased with increases in the number of trials (FIG. 10E). This indicates that motor learning ability controlled by the cerebellum also rescued by CRAG or VCP (C522T) expression.

Figure 11:
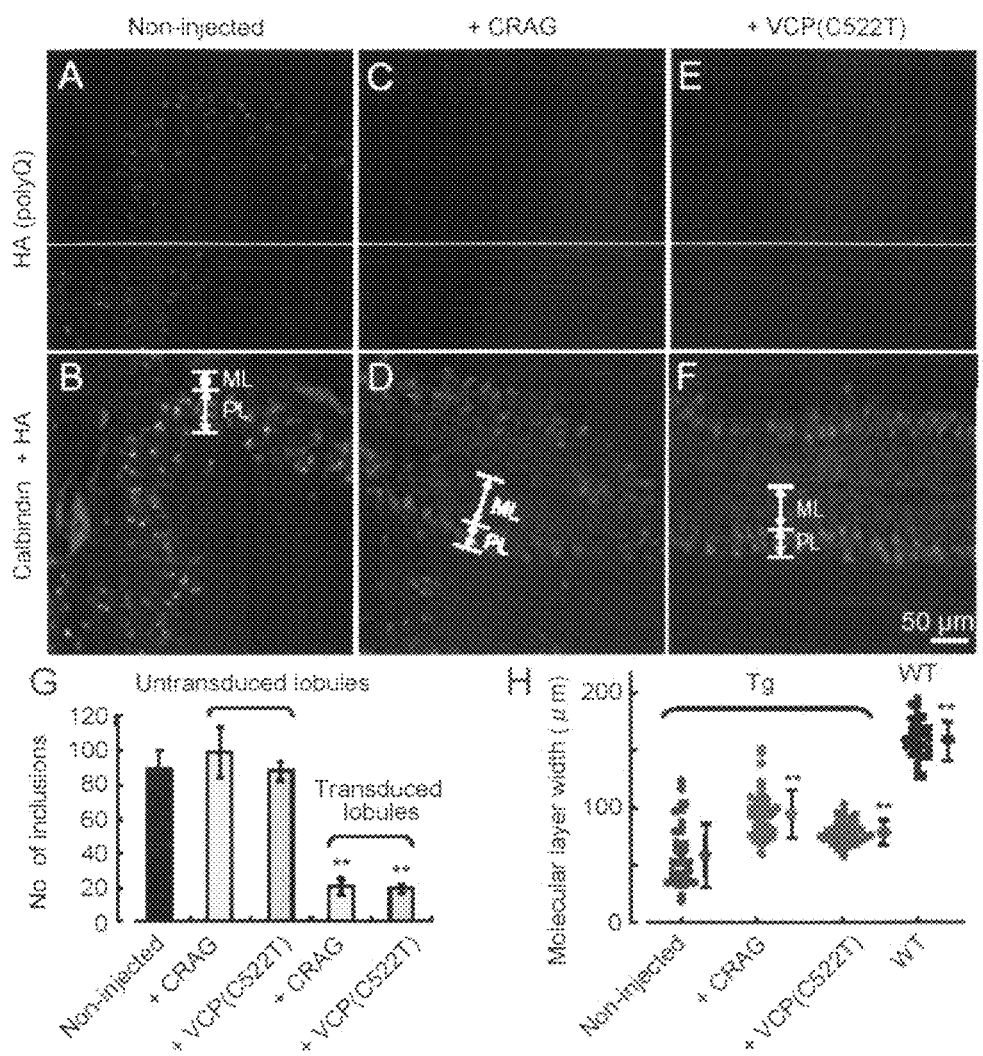
FIG. 11 shows the immunohistological staining, with an anti-HA tag antibody, of cerebellar slices prepared by perfusion fixation from non-injected (A and B) mice or 8 weeks after injection of a CRAG-(C and D) or VCP (C522T) (E and F)-expressing virus (A, C, and E), and shows the image thereof overlaid on an image of double immunohistological staining with an anti-calbindin antibody (B, D, and F).

2 months after viral vector injection, the mice of the b line were subjected to perfusion fixation, and their cerebellar slices were prepared. The cerebellar slices were double immunohistological-stained with an anti-HA tag antibody (FIGS. 11A, 11C, and 11E) and an anti-calbindin antibody (FIGS. 11B, 11D, and 11F). A Purkinje cell layer in non-expressing slices exhibited large disturbances and observed to intracellularly have inclusions containing ataxin-3 (FIGS. 11A and 11B). By contrast, in the CRAG- or VCP (C522T)-expressing slices, most of inclusions disappeared, and monolayer or double layer arrangement of Purkinje cells was observed and were close to that observed in wild-type mice (FIGS. 11C to 11F). The number of inclusions in the cerebellar cortex (FIG. 11G) and the thickness of a molecular layer in the cerebellar cortex (FIG. 11H) were measured. As a result, the CRAG- or VCP (C522T)-expressing slices were observed to have significant reduction in the number of inclusions and significant increase in the thickness of a molecular layer.

Example 8

Figure 12:
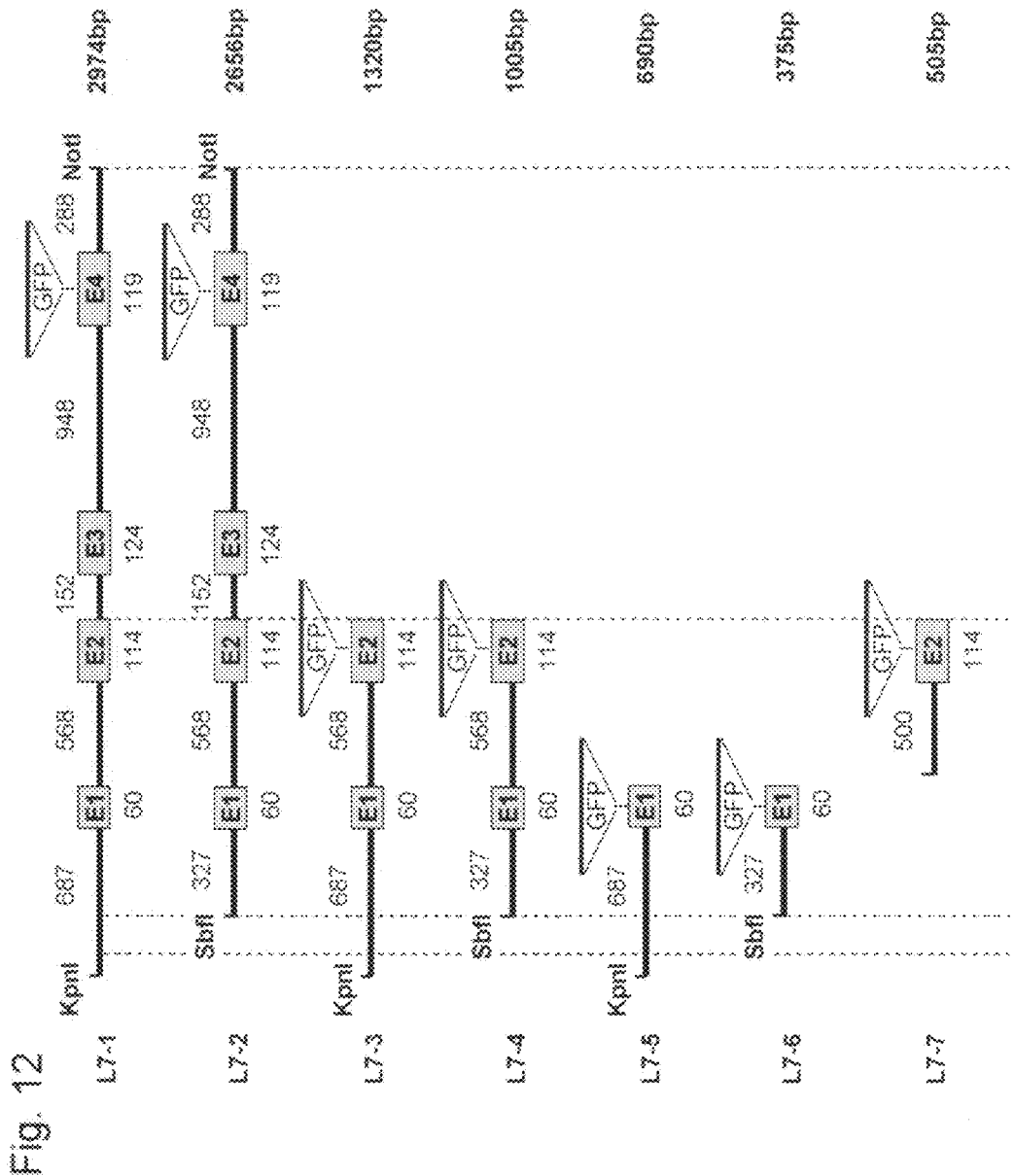
FIG. 12 is a schematic diagram showing the structures of an L7 promoter (L7-1) and various kinds of modified L7 promoters (L7-2 to L7-7).

As shown in FIG. 12, various truncated L7 promoters (L7-2, L7-3, L7-4, L7-5, L7-6, and L7-7) were prepared based on a conventional L7 promoter (L7-1). GFP was expressed under the control of these truncated promoters using a lentiviral vector and Purkinje cell selectivity was compared between the truncated promoters and a CMV promoter, an MSCV promoter, or the conventional L7 promoter (L7-1). The sequences of L7-1 to L7-7 are shown in SEQ ID NOs: 1 to 7, respectively, in the Sequence Listing.
<Methods>
(1) Virus Generation The following procedures were performed in a P2 laboratory. HEK293FT cells were used in virus generation. As a culture medium, a conventional Dulbecco's modified Eagle's medium (D-MEM) supplemented with 10% bovine serum was used. HEK293FT cells in log phase growth were dispersed in a phosphate-buffered saline ($Mg^{2+}$- and $Ca^{2+}$-free) [PBS(−)] and subsequently plated onto a 10-cm dish (Falcon) at a density of $5 \times 10^5$ cells per dish. To the 10-cm dish after plating, 10 ml of D-MEM containing 10% by weight of fetal bovine serum was added, and the cells were then cultured at 5% (by volume) $CO_2$ at 37° C. 24 hours later, the culture medium in the dish was replaced by 10 ml of a fresh culture medium (D-MEM containing 10% by weight of fetal bovine serum). Then, the cells were cultured at 5% (by volume) $CO_2$ at 37° C. for 0.5 hours.

Figure 13:
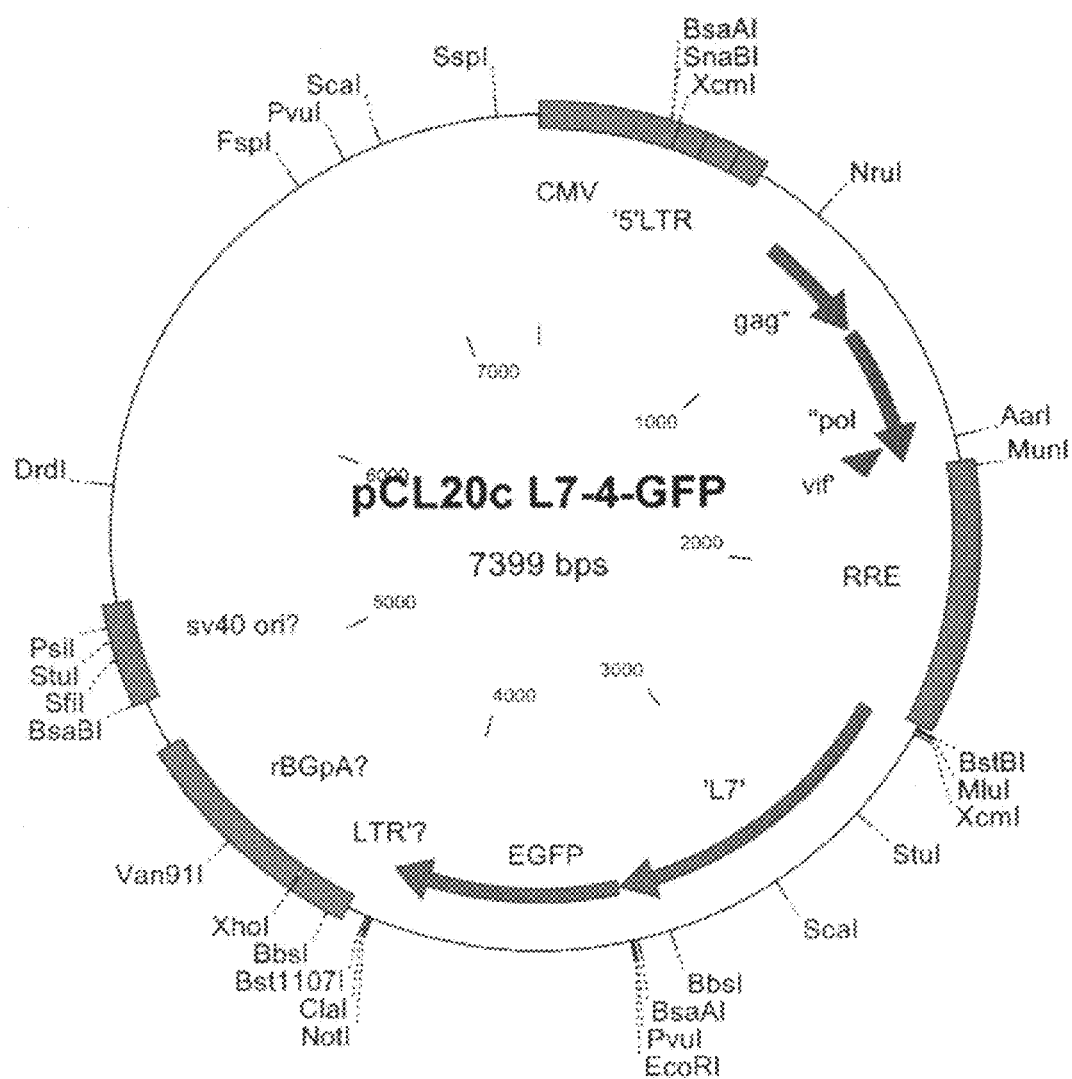
FIG. 13 is a schematic diagram of a plasmid pCL20c L7-4-GFP obtained by inserting an L7-4 promoter to a lentiviral vector plasmid (pCL20c) and locating a GFP (green fluorescent protein) gene downstream thereof.

The following plasmids: 6 μg of pCAGkGP1R (St. Jude Children's Research Hospital), 2 μg of pCAG4RTR2 (St. Jude Children's Research Hospital), 2 μg of pCAG-VSV-G (St. Jude Children's Research Hospital), and 10 μg of pCL20c L7-X-GFP or pCL20c MSCV-GFP (St. Jude Children's Research Hospital/George Washington University) were separately dissolved in 450 μl of sterilized water to obtain plasmid solutions.

pCAGkGP1R: a packaging plasmid containing gag (encoding viral structural proteins) and pol (encoding reverse transcriptase).

pCAG4RTR2: a plasmid containing tat (transcriptional control gene). The virion cannot replicate in hosts due to the deletion of rev.

pCAG-VSV-G: VSV-G is an abbreviation of a vesicular stomatitis virus glycoprotein. A lentivirus having the original envelope can infect only CD4-positive cells. The plasmid can infect various cells including neurons by substituting the original envelope by an envelope of VSV (vesicular stomatitis virus) which is targeting to phospholipid (phosphatidylserine) serving as a component of cell membranes.

pCL20c MSCV-GFP: a plasmid which has an MSCV promoter substituted for a promoter of a main vector pCL20c of a lentivirus and has a GFP gene linked within two LTRs (FIG. 1).

pCL20c L7-X-GFP: a plasmid which has the L7 promoter (L7-1) or the truncated promoters (L7-2 to L7-7) thereof substituted for a promoter of a main vector pCL20c of a lentivirus and has a GFP gene linked within two LTRs (the structure of pCL20c L7-4-GFP is shown in FIG. 13, and the complete sequence thereof is shown in SEQ ID NO: 8 in the Sequence Listing).

To the obtained plasmid solutions, 50 μl of 2.5 M $CaCl_2$ was added, and the mixture was stirred. 500 μl of 2×HBSS [composition: 50 mM HEPES, 0 mM NaCl, 1.5 mM $Na_2HPO_4$, pH 7.05] was added to the mixture and stirred immediately.

The plasmid solutions were aliquoted dropwise to the dish and gently mixed with the medium in the dish. Then, the cells were cultured at 5% (by volume) $CO_2$ at 35° C. Subsequent procedures were performed in a biological safety cabinet.

16 hours later, the medium in the dish was replaced by 10 ml of a fresh medium (D-MEM containing 10% by weight of fetal bovine serum). The cells were further cultured at 5% (by volume) $CO_2$ at 37° C. The virus-containing culture medium was harvested 40 hours after transfection (40 h virus).
(2) Condensation Each medium collected in the paragraph (1) was transferred to a 50-ml centrifuge and centrifuged at 1000 rpm (120×g) for 4 minutes to obtain a supernatant. The obtained supernatant was filtered through a filter (Millipore, 0.22 μm in pore size). The obtained filtrate was subjected to ultracentrifugation (25,000 rpm, 2 hours, 4° C.) using a rotor SW28.1 manufactured by Beckman Coulter to precipitate viral particles. The supernatant was removed.

The obtained viral particle pellets were suspended in PBS (−) to obtain a virus solution for infection in a final amount of 200 μl. The virus solution which was not immediately used was dispensed in 20 μl aliquots and stored at −80° C.

(3) Titration of Virus

A virus titer was evaluated based on the copy number of provirus incorporated into the genomes of cultured cells (HeLa cells) (Izopet et al. J Med. Virol. 1998 January; 54 (1): 54-9). HeLa cells were cultured in 10-cm dishes and infected with the virus solution 24 hours after plating. 3 days after the infection, $5.0 \times 10^6$ cells were harvested. In parallel with this, the equivalent number of LAV-8E5 cells (ATCC, Manassas, Va., USA) were prepared. The LAV-8E5 cells, which have 1 copy of HIV type 1 provirus per cell, were used as a standard. Genomic DNA was extracted from these cells and finally suspended in 100 μl of TE buffer. A 290-bp region contained in RRE (rev responsive element) of the HIV provirus was amplified using 1 μl aliquot of the genomic DNA solution and the following primers:

```
5'-ATGAGGGACAATTGGAGAAGTGAATTA-3'   (SEQ ID NO: 9)
and

5'-CAGACTGTGAGTTGCAACAGATGCTGT-3'.  (SEQ ID NO: 10)
```

The copy number incorporated into the genome was determined by limiting dilution of the genomic DNA. Specifically, a dilution ratio was determined immediately before no bands were observed, and compared with the standard using the LAV-8E5 cells to determine the copy number of provirus incorporated per $5.0 \times 10^6$ HeLa cells (the genomic copy number/ml virus solution).

(4) Experiment of Gene Transfer to Cultured Cerebellar Purkinje Cells

Culture was conducted in a 12-well dish according to the following procedures using the cerebellums of Wistar rats on embryonic day 20 or 21: a cerebellar cell suspension with a density of $1.0 \times 10^7$ cells/ml was prepared using DMEM/F12 containing 10% FBS. The suspension was spread in an amount of 20 μl/well (corresponding to about 200,000 cells) over a plastic cover slip (SUMITOMO BAKELITE Co., Ltd., Sumilon MS-80060) of 13 mm in diameter (previously coated with poly-L-ornithine) to form a thin layer of approximately 6 mm in diameter. Then, the cover slip was left standing for 2 hours in a humidified incubator kept at 5% $CO_2$ at 37° C. The cells were attached to the cover slip. Then, the supernatant was removed by aspiration, and 800 μl of a culture medium (the following components) warmed to 37° C. was added to the cover slip. Components in the culture medium: DMEM-nutrient mixture of Ham's F-12 (Sigma)+ bovine insulin (10 mg/ml), bovine serum albumin (100 mg/ml), gentamicin (5 mg/ml), glutamine (200 mg/ml), human apotransferrin (100 mg/ml), progesterone (40 nM), putrescine (100 nM), sodium selenite (30 nM), and triiodothyronine (0.5 ng/ml). Next, 1 ml of the virus solution having a titer of 2 to $4 \times 10^5$ genomic copies/ml was added thereto for infection. On the next day (24 hours later), FBS was added thereto at a final concentration of 1%.

14 days later, GFP fluorescence images of the cultured cells were taken. 40 Purkinje cells were randomly selected, and an average of their fluorescence intensities was measured. Evaluation was conducted using average GFP fluorescence intensity obtained using a CMV promoter as 100%.

(5) Injection of Vector to Subarachnoid Space in Mouse Cerebellum

Mice (supplied from SLC, 4 to 10 weeks old) were anesthetized by intraperitoneal administration (40 mg/kg body weight) of pentobarbital (trade name: Nembutal). The following procedures were performed in a biological safety cabinet.

After anesthesia, the mice were fixed using a small animal stereotaxic apparatus (manufactured by NARISHIGE, trade name: SG-4). Moreover, the body temperatures of the mice were kept at 37° C. using a body temperature controller (manufactured by FST, trade name: Body Temperature Control System (for mice) FST-HPSM). Hair on the mouse heads was clipped. Then, the skin was incised from a few millimeters rostral to bregma to directly above the cerebellum. Subsequently, a hole of 2 to 3 mm in interior diameter was made in the skull at the midline 5 to 7 mm caudal to bregma using a microdrill (Urawa Corp., trade name: Power Controller UC100+HB1 (drill)) under a stereoscopic microscope (Nikon Corp., trade name: 1SMZ645). Moreover, a hole was made in the dura mater and arachnoid mater beneath the bone using an injection needle.

The obtained lentiviral vector was charged to a Flexifil microsyringe (trade name, manufactured by WPI, 10 μl volume), and the Flexifil microsyringe was set in Ultramicropump 2 (manufactured by WPI) attached to a micromanipulator.

The needle tip of the microsyringe was inserted approximately 0.5 mm through the hole in the dura mater made directly above the cerebellum and placed in the subarachnoid space. Then, the obtained lentiviral vector was injected at a dose of 4 μl in total at a speed of 100 nl/minute for 40 minutes using an Ultramicropump 2-specific digital controller Micro 4 (trade name, manufactured by WPI).

After injection, the incised mouse skin was sutured with an opthalmological microneedle with threads (manufactured by Natsume Seisakusho Co., Ltd., trade name: Opthalmological Slightly Curved Needle C67-0). Then, the mice were removed from the stereotaxic apparatus and observed in a cage (in the safety cabinet) placed on a heating pad (Showa Mold & Engineering Co., Ltd., trade name: Rubber Mat Heater SG-15). The mice were awakened from anesthesia and then raised in the mouse cage placed in a rack with an HEPA filter for infected animals (Tokiwa Kagaku Kikai Co., Ltd., trade name: Bio Clean Capsule Unit T-BCC-M4).

7 days after injection, the mice were subjected to perfusion fixation with 4% formaldehyde-phosphate buffer, and the brains were excised. Imagehs of the whole brains and fluorescence images of GFP were taken using a fluorescence stereoscopic microscope. Then, sagittal sections of the cerebellums of 50 μm or 100 μm in thickness were prepared using a microslicer (Dosaka EM, trade name: DTK-1000). The prepared brain sections were incubated at room temperature for 24 hours with a primary antibody [mouse monoclonal anti-parvalbumin (marker for stellate cells and basket cells) manufactured by SIGMA, mouse monoclonal anti-GFAP (marker for glial cells) manufactured by Chemicon, mouse monoclonal anti-neuron-specific nuclear protein (NeuN, marker for granule cells) manufactured by Chemicon, or mouse monoclonal anti-mGluR2 (marker for Golgi cells) donated from Professor R. Shigemoto, National Institute for Physiological Sciences] and subsequently incubated at room temperature for 2 hours with a secondary antibody (Alexa Fluor 568-conjugated anti-mouse IgG manufactured by Invitrogen) to obtain samples for microscopic examination. Then, the localization of GFP proteins expressed and the types of GFP-expressing cells were examined by observing the samples using a fluorescence microscope (Leica, trade name: DMI 6000B) and a confocal microscope (CarlZeiss, trade name: LSM5 Pascal).

<Results>

FIG. 14 shows an introduction rate (expression rate) in cultured cerebellar neurons when GFP is expressed under the control of various kinds of promoters using the lentiviral vector. FIG. 14A shows the proportion of GFP-expressing Purkinje cells to all GFP-expressing cells: the number of GFP-expressing Purkinje cells/the number of GFP-expressing cells. When a CMV or MSCV promoter was used, cells other than Purkinje cells occupied most of the GFP-expressing cells. By contrast, when L7-1 to L7-4 were used, gene expression was found only in Purkinje cells. When L7-5 and L7-6 were used, GFP-expressing cells were absent. When L7-7 was used, specificity for Purkinje cells was lower, and cells other than Purkinje cells occupied approximately a half of GFP-expressing cells. FIG. 14B shows the proportion of GFP-expressing Purkinje cells to all Purkinje cells: the number of GFP-expressing Purkinje cells/the number of all Purkinje cells. When a CMV promoter was used, GFP expression was observed only in approximately ⅕ of all Purkinje cells. When L7-1 was used, GFP expression was observed only in approximately ⅓ of all Purkinje cells. By contrast, when L7-4 was used, GFP was expressed in almost 100% Purkinje cells, i.e., all existing Purkinje cells. The results shown are an average obtained using cultured cerebellar neuron samples in at least 4 independent experiments. Moreover, the viral vectors used had almost the same titers (2 to $4\times10^5$ genomic copies/ml).

Figure 15:
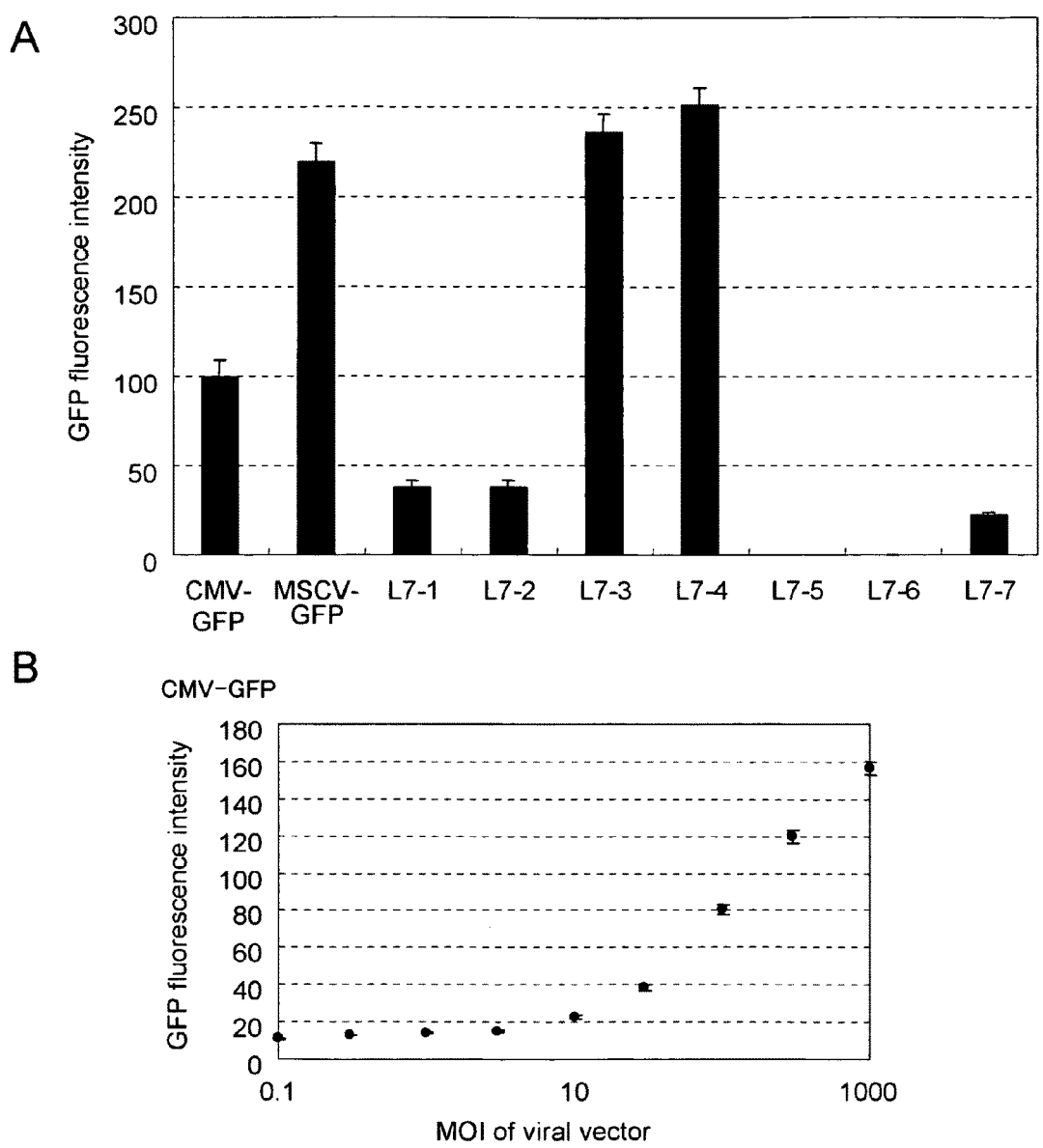
FIG. 15A shows the comparison of fluorescence intensity of GFP expressed by cultured cerebellar Purkinje cells using lentiviral vectors inserted therein various promoters.
FIG. 15B shows GFP fluorescence intensity from HEK293T cells infected at various MOIs with a lentiviral vector expressing GFP under the control of a CMV promoter.

FIG. 15A shows fluorescence intensity of GFP expressed by cultured cerebellar Purkinje cells under the control of various kinds of promoters using the lentiviral vector. 40 Purkinje cells were randomly selected, and fluorescence images thereof were captured with a cooled CCD camera. Then, fluorescence intensity was measured using IPLab imaging software (Scanalytics). FIG. 15B is a graph showing GFP fluorescence intensity from HEK293T cells infected at various MOIs with a lentiviral vector expressing GFP under the control of a CMV promoter. Forty HEK293T cells were randomly selected, and fluorescence intensity was measured using IPLab imaging software. The fluorescence intensity was almost proportional to an MOI log from MOI 10 through 1000.

Figure 16:
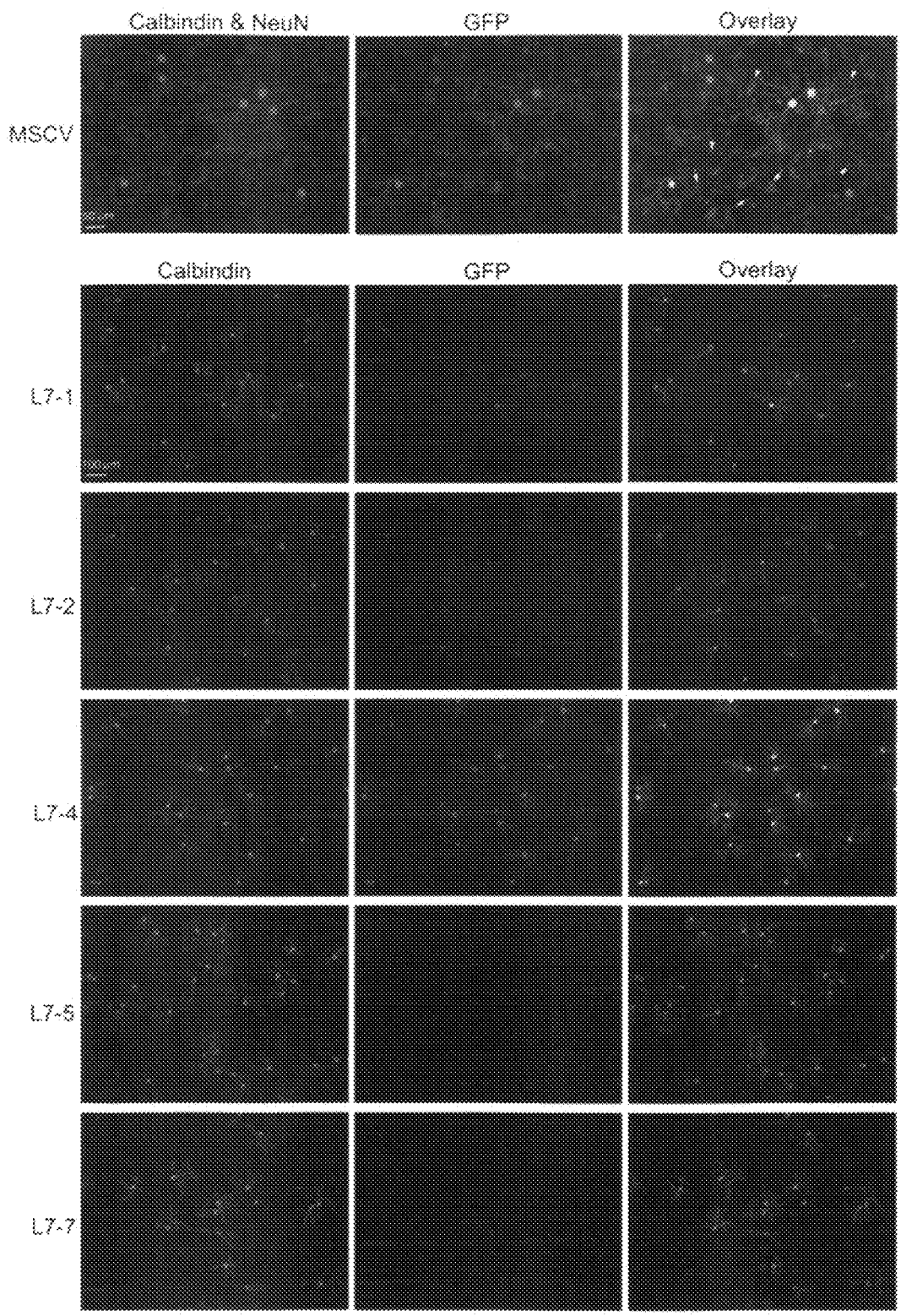
FIG. 16 shows a fluorescence immunostaining photograph of a GFP gene expressed in cultured cerebellar Purkinje cells using lentiviral vectors inserted therein various promoters.

FIG. 16 shows results of GFP expression in cultured cerebellar Purkinje cells under the control of an MSCV promoter, the conventional L7 promoter (L7-1), or the truncated promoters (L7-2, L7-4, L7-5, or L7-7) using the lentiviral vector. The left panels respectively show a photograph of fluorescence immunostaining with a Purkinje cell-specific anti-calbindin antibody. Only when an MSCV promoter was used (upper left panel), the samples were stained with the anti-calbindin antibody in combination with a granule cell-specific anti-NeuN antibody (both Purkinje cells and granule cells appear red). The center panels respectively show a fluorescence photograph of GFP expressed by each viral vector. The right panels respectively show the left panels overlaid on the center panels. When an MSCV promoter was used, GFP expression was observed not only in Purkinje cells and granule cells but also in glial cells (arrows) and cells (arrowheads) with intermediate size between granule cells and Purkinje cells. By contrast, when L7-1, L7-2, and L7-4 were used, GFP expression was observed only in Purkinje cells. Particularly, when L7-4 was used, GFP was expressed in all existing Purkinje cells and furthermore, was strongly expressed therein, demonstrating that its promoter activity is much higher than that of conventional L7-1.

FIG. 17 shows results of an experiment of gene expression in the mouse cerebellum using lentiviral vectors incorporating therein various kinds of promoters. FIGS. 17A to 17D are respectively a fluorescence photograph of GFP expressed under the control of the conventional L7 promoter (L7-1) using the lentiviral vector (titer: $3.7\times10^5$ genomic copies/ml). FIGS. 17C and 17D are respectively a photograph of immunostaining with an anti-GFP antibody (this enhances fluorescence). FIGS. 17E to 17H are respectively a fluorescence photograph of GFP in cerebellar Purkinje cells obtained using a lentiviral vector having L7-4 instead of the conventional L7-1 promoter (titer: $2.4\times10^5$ genomic copies/ml). The use of L7-4 was confirmed to produce a much higher number of GFP-expressing Purkinje cells and GFP expression level than those produced by the use of L7-1 even though almost the same titers (at which almost the same copy number of provirus is introduced into chromosomes) are used.

All publications, patents, and patent applications cited herein are incorporated herein by reference in their entirety.

INDUSTRIAL APPLICABILITY

According to the present invention, a vector having high selectivity for cerebellar Purkinje cells can be prepared without the use of serum. The vector of the present invention can be utilized widely from basic research to clinical application in the neuroscience field, such as the elucidation of, at a molecular level, mechanisms of motor learning or motor coordination controlled by the cerebellum and the gene therapies of Purkinje cell-affecting disease, for example, spinocerebellar ataxia.

FREE TEXT FOR THE SEQUENCE LISTING

SEQ ID NO: 1: L7-1
SEQ ID NO: 2: L7-2
SEQ ID NO: 3: L7-3
SEQ ID NO: 4: L7-4
SEQ ID NO: 5: L7-5
SEQ ID NO: 6: L7-6
SEQ ID NO: 7: L7-7
SEQ ID NO: 8: pCL20c L7-4-GFP
SEQ ID NO: 9: description of artificial sequence: primer
SEQ ID NO: 10: description of artificial sequence: primer

The invention claimed is:

1. A cerebellar Purkinje cell-tropic vector comprising a L7 promoter operably linked to a foreign gene operably linked to a virus-based plasmid vector, wherein the L7 promoter is selected from the group consisting of:
 a) a DNA consisting of the nucleotide sequence shown in SEQ ID NO:3,
 b) a DNA consisting of the nucleotide sequence shown in SEQ ID NO:4, and
 c) a DNA consisting of a nucleotide sequence fragment of SEQ ID NO:3 that contains at least the nucleotide sequence of 317 to 1322 of SEQ ID NO: 1.

2. The vector according to claim 1, wherein the virus is selected from an adenovirus, an adeno-associated virus, a retrovirus, a herpesvirus, a Sendai virus, and a lentivirus.

3. The vector according to claim 1, wherein the virus is a lentivirus.

4. The vector according to claim 1, wherein the vector is produced in a culture medium comprising a protease inhibitor to inhibit degradation of a viral protein.

5. The vector according to claim 4, wherein the viral protein is a glycoprotein present on the viral envelope.

6. The vector according to claim 4, wherein the protease inhibitor has a cathepsin K inhibitory activity.

7. The vector according to claim 1, wherein the vector is produced in a culture medium at pH 7.2 to pH 8.0.

8. The vector according to claim 1, wherein the vector is produced in a serum-free culture medium.

9. The vector according to claim 1, wherein the foreign gene is a therapeutic gene for Purkinje cell-affecting disease or a disease gene for the disease.

10. The vector according to claim 9, wherein the therapeutic gene is any one or more selected from genes encoding molecular chaperones including GTPase CRAG, ubiquitin chain assembly factor E4B (UFD2a), ATPase VCP/p97, HDJ-2, HSDJ, and BiP, apoptosis suppressors including YAP-deltaC, endoplasmic reticulum protein degradation-promoting molecules including ER degradation enhancing alpha-mannosidase-like protein (EDEM), ER sensor molecules including CREB/ATF family members OASIS, IRE1, PERK, and ATF6, sphingomyelinase, AT-mutated (atm), Reelin, Bcl-2, neprilysin, BDNF, and NGF, or siRNA(s) for any one or more selected from genes encoding ataxin-1, ataxin-2, ataxin-3, voltage-dependent calcium channel ala subunit, and PKCγ.

11. The vector according to claim 9, wherein the disease gene is any one or more selected from genes with an abnormally expanded CAG repeat that encode ataxin-1, ataxin-2, ataxin-3, huntingtin, and voltage-dependent calcium channel α1a subunit, and a gene encoding PKCγ having a mutation.

12. A pharmaceutical composition for the treatment of cerebellar Purkinje cell-affecting disease comprising a vector according to claim 1, wherein the vector comprises the modified L7 promoter operably linked to a therapeutic gene for Purkinje cell-affecting disease.

13. The pharmaceutical composition according to claim 12, wherein the cerebellar Purkinje cell-affecting disease is any one selected from polyglutamine disease including spinocerebellar ataxia and Huntington disease, Niemann-Pick disease, ataxia-telangiectasia, autism, Alzheimer's disease, fetal alcohol syndrome, alcoholism, and age-related cerebellar ataxia.

14. A non-human mammal comprising a vector according to claim 1 introduced thereinto.

15. The non-human mammal according to claim 14, wherein the vector comprises the modified L7 promoter operably linked to one or more genes selected from the group consisting of genes with an abnormally expanded CAG repeat that encode ataxin-1, ataxin-2, ataxin-3, huntingtin, and voltage-dependent calcium channel a1a subunit, and a gene encoding PKCγ having a mutation.

16. A method for preparing a cerebellar Purkinje cell-tropic virus, the method comprising:
   i) introducing the cerebellar Purkinje cell-tropic vector of claim 1 into a host cell;
   ii) culturing the host cell of (i) in a culture medium comprising a protease inhibitor; and
   iii) isolating the cerebellar Purkinje cell-tropic virus from the culture medium.

17. The method according to claim 16, wherein the protease inhibitor has a cathepsin K inhibitory activity.

18. The method according to claim 16 or 17, wherein the culture medium has pH 7.2 to pH 8.0.

19. The method according to claim 16 or 17, wherein the culture medium is serum-free.

\* \* \* \* \*

SEQUENCE LISTING

```
<160> NUMBER OF SEQ ID NOS: 10

<210> SEQ ID NO 1
<211> LENGTH: 2974
<212> TYPE: DNA
<213> ORGANISM: Mus musculus
<220> FEATURE:
<223> OTHER INFORMATION: L7-1 (L7 promoter)

<400> SEQUENCE: 1
```

```
tcagagcatg gtcagaaagc cacagctcat caatgaaatg gtcagggact tcctgtcctg    60
ctccatgcat aaatgaaaga cgaagacaac tcaaattggc atttgagggg cagataaaca   120
ggagcatccg gtagtttcac aggtggtcgg gtagcaggag ccgggttggt tggttggtct   180
gtggagagtg cagggattaa gggaagaggc ctggacccca acttcttcct tggctacccc   240
cctgaaaatg tcacctgcct tgcatggacg aactcacagg caggaatggg ttggcttggg   300
tggggacatc ctgcaggttc caccctcatg ttggttcatc ttcaacattg tactgacttc   360
ttcccacttg acattcctca aggtcctgtg atcatggctg ggtctagtga ggttcaaacc   420
tgcactgccc tacccacacc cacacccagc tcagcgtcag tcaggatcaa caattaccta   480
gagatcatct ttctggggct taagcattgg tgggagcaga tgggatatga gctggggatt   540
tgggaatggg ggaagatatc tgctccccct cccctacac cctagccttt taaaaggcct    600
tctcaggtca gagaccagga gaaaagtata ggagagatac acaatggacc aggaagaaga   660
aaagggagag ggaggctcag accttctaga caaggtaaga gggctctggc tgactccacc   720
atccgcttct tgaggtctcg gcacctgtaa ttgacaagat taattcattt ataggggcatc   780 taattagcaa gcaagtctct ggagtcccct gacccagtta ctataacaca caggggtat    840 aggtaggaga gtataagagc ccctcctcag ggcaaatgaa tggattctta gtactgtccc   900
ccaagagata gtaggtacta ggatttaggg gcacttctga gccccatttc cctggtaagt   960
gtcccaaccc cccaaatcaa cccaagcctg gtctcaatct aggacagtgg tagaatgctg  1020
tccctagagt cagtaccatg tgaaattgtg ctgcaggcag ggcccccagg ctgggaggtg  1080
ggggttgggg gagtcagggc aggtcaggga aggagactca ggtttcattt agagaaattc  1140
tgcagacccg tgaggactat ggtgagagca gagatgggaa ggcaggcact gtttcgggtg  1200
gatgctgtct ggaagacagg gaaggcacag accaaactaa accaatcacg tctgtcccca  1260
aggcaggttc accggaccag gaaggcttct tcaacctgct gacccacgtg cagggcgatc  1320
ggaaggagga gcagcgctgt tccttgcagg ctgggccagg ccagaaccca gaaagccgta  1380
agcagggcgt gattgggccg tgtgtgtgtg tgtgtgtgtg tgtgtgtgtg tgtgtgtgtg  1440
tggcaggagt gctggggttc tgggatcttg tggatcttgg gactcaggat ggggtctgta  1500
ttcatgcctg cctgtctctg ctccaagcag agggtggccc tgctccagag aaggacaatc  1560
tcaaggataa gctggtcaac acccagggcc gccgcaagga cgaccagcgt gtaacagtta  1620
attccctgcc tggcttccaa cctatcggcc ccaaggtagg tgatgtccag attacctgtg  1680
agactccaca tagctctcta aatctatgac ctgtctctag gcaggaaagg agaggaccct  1740
atgaacacgt aaagtgctat gggcttaagg tcaggtggca ggactcatgc tagtgcagaa  1800
ctatggctga aaattacagt tcctgctcca acatctgtat atttgggaga ggccacaggg  1860
agaaaacagg cagttttcct ggaaggcata tgaatgcata ccctataaa tcaatgaaga  1920 gtagggcttc tgtttgggag tgttttgctt tattgttttt gagacagggt ttcatgtagc  1980
tctggctggc atgttctcct acatgtgcat cctgggttct gggataacag gtgtgagtca  2040
ccatgagtga tgtatgtggg tagggataga acccagggct tgatgcagt ctctatcaac   2100 tgagctccag ccccagccct atgtctgtgt acattagcat acatgtttag agctccgggc  2160
acacgtgtgc acacgcaggt ggaggccaga agtcaatctc ctgccctggg agctttcagt  2220
gccctggaac tccaggtaga tcaggctctc tagctaggaa gcccttggta tcctcctgac  2280
tcttaagcac tgagattaca agtgcataaa cccacacctg gcttaaactc aggtcttcaa  2340
```

| | |
|---|---:|
| atgagcatag caaggatttc aatgactgag ctatcttctc aactcaactg tttgtttgtt | 2400 |
| tgttttagta tttagctttg aactcaaaat aatcctcctg cctgtttctt gagtactggg | 2460 |
| attacaggta tacactaaca ggccaatgtc tgaccaaata ccaccaccct aattagcaga | 2520 |
| cgaaaaaaaa acattgtttg gaggcacttc tgacttgcac tttccttggt cccctccctc | 2580 |
| cgtctgaccc ttcttcatcc ccaggatgga atgcagaaac gacctgggac cctcagccct | 2640 |
| caaccectgc tcacccctca ggatcctgct gcactcagct tccgcaggaa cagcagcccc | 2700 |
| cagccccaga cacaagctcc ttgagagttc tagccatcct gggcctccca ctggcccctg | 2760 |
| aaaacaataa aacacttggc actagcaaca aagagttgag tgtgtgttat tttctgtggt | 2820 |
| ggggaaggga gctgggactt gaggaactga aggtctcagg agctctgctg ggcagcttga | 2880 |
| agaagtctct cttctttctg cttccggatc ttctgcttaa attcttctag ctcctggcgc | 2940 |
| tggaatgggg aaagggggtgt gatgggaagg aatt | 2974 |

<210> SEQ ID NO 2
<211> LENGTH: 2656
<212> TYPE: DNA
<213> ORGANISM: Mus musculus
<220> FEATURE:
<223> OTHER INFORMATION: L7-2

<400> SEQUENCE: 2

| | |
|---|---:|
| gttccaccct catgttggtt catcttcaac attgtactga cttcttccca cttgacattc | 60 |
| ctcaaggtcc tgtgatcatg gctgggtcta gtgaggttca aacctgcact gccctaccca | 120 |
| cacccacacc cagctcagcg tcagtcagga tcaacaatta cctagagatc atctttctgg | 180 |
| ggcttaagca ttggtgggag cagatgggat atgagctggg gatttgggaa tgggggaaga | 240 |
| tatctgctcc ccctccccct acaccctagc cttttaaaag gccttctcag gtcagagacc | 300 |
| aggagaaaag tataggagag atacacaatg gaccaggaag aagaaaaggg agagggaggc | 360 |
| tcagaccttc tagacaaggt aagagggctc tggctgactc caccatccgc ttcttgaggt | 420 |
| ctcggcacct gtaattgaca agattaattc atttataggg catctaatta gcaagcaagt | 480 |
| ctctggagtc ccctgaccca gttactataa cacacagggg gtataggtag gagagtataa | 540 |
| gagcccctcc tcagggcaaa tgaatggatt cttagtactg tcccccaaga gatagtaggt | 600 |
| actaggattt aggggcactt ctgagcccca tttccctggt aagtgtccca accccccaaa | 660 |
| tcaacccaag cctggtctca atctaggaca gtggtagaat gctgtcccta gagtcagtac | 720 |
| catgtgaaat tgtgctgcag gcaggggccc caggctggga ggtgggggtt ggggagtca | 780 |
| gggcaggtca gggaaggaga ctcaggtttc atttagagaa attctgcaga cccgtgagga | 840 |
| ctatggtgag agcagagatg ggaaggcagg cactgtttcg ggtggatgct gtctggaaga | 900 |
| cagggaaggc acagaccaaa ctaaaccaat cacgtctgtc cccaaggcag gttcaccgga | 960 |
| ccaggaaggc ttcttcaacc tgctgaccca cgtgcagggc gatcggaagg aggagcagcg | 1020 |
| ctgttccttg caggctgggc caggccagaa cccagaaagc cgtaagcagg gcgtgattgg | 1080 |
| gccgtgtgtg tgtgtgtgtg tgtgtgtgtg tgtgtgtgtg tgtgtggcag gagtgctggg | 1140 |
| gttctgggat cttgtggatc ttgggactca ggatggggtc tgtattcatg cctgcctgtc | 1200 |
| tctgctccaa gcagagggtg gccctgctcc agagaaggac aatctcaagg ataagctggt | 1260 |
| caacacccag ggccgccgca aggacgacca gcgtgtaaca gttaattccc tgcctggctt | 1320 |
| ccaacctatc ggccccaagg taggtgatgt ccagattacc tgtgagactc cacatagctc | 1380 |
| tctaaatcta tgacctgtct ctaggcagga aaggagagga ccctatgaac acgtaaagtg | 1440 |

```
ctatgggctt aaggtcaggt ggcaggactc atgctagtgc agaactatgg ctggaaatta 1500
cagttcctgc tccaacatct gtatatttgg gagaggccac agggagaaaa caggcagttt 1560
tcctggaagg catatgaatg catacccta taaatcaatg aagagtaggg cttctgtttg 1620
```

```
ggagtgtttt gctttattgt ttttgagaca gggtttcatg tagctctggc tggcatgttc 1680
tcctacatgt gcatcctggg ttctgggata acaggtgtga gtcaccatga gtgatgtatg 1740
tgggtaggga tagaacccag ggctttgatg cagtctctat caactgagct ccagccccag 1800
ccctatgtct gtgtacatta gcatacatgt ttagagctcc gggcacacgt gtgcacacgc 1860
aggtggaggc cagaagtcaa tctcctgccc tgggagcttt cagtgccctg gaactccagg 1920
tagatcaggc tctctagcta ggaagccctt ggtatcctcc tgactcttaa gcactgagat 1980
tacaagtgca taaacccaca cctggcttaa actcaggtct tcaaatgagc atagcaagga 2040
tttcaatgac tgagctatct tctcaactca actgtttgtt tgtttgtttt agtatttagc 2100
tttgaactca aaataatcct cctgcctgtt tcttgagtac tgggattaca ggtatacact 2160
aacaggccaa tgtctgacca aataccacca ccctaattag cagacgaaaa aaaaacattg 2220
tttggaggca cttctgactt gcactttcct tggtcccctc cctccgtctg acccttcttc 2280
atccccagga tggaatgcag aaacgacctg ggaccctcag ccctcaaccc ctgctcaccc 2340
ctcaggatcc tgctgcactc agcttccgca ggaacagcag cccccagccc cagacacaag 2400
ctccttgaga gttctagcca tcctgggcct cccactggcc cctgaaaaca ataaaacact 2460
tggcactagc aacaaagagt tgagtgtgtg ttattttctg tggtggggaa gggagctggg 2520
acttgaggaa ctgaaggtct caggagctct gctgggcagc ttgaagaagt ctctcttctt 2580
tctgcttccg gatcttctgc ttaaattctt ctagctcctg gcgctggaat ggggaaaggg 2640
gtgtgatggg aaggaa 2656

<210> SEQ ID NO 3
<211> LENGTH: 1322
<212> TYPE: DNA
<213> ORGANISM: Mus musculus
<220> FEATURE:
<223> OTHER INFORMATION: L7-3

<400> SEQUENCE: 3
tcagagcatg gtcagaaagc cacagctcat caatgaaatg gtcagggact tcctgtcctg 60
ctccatgcat aaatgaaaga cgaagacaac tcaaattggc atttgagggg cagataaaca 120
ggagcatccg gtagtttcac aggtggtcgg gtagcaggag ccgggttggt tggttggtct 180
gtggagagtg cagggattaa gggaagaggc ctggacccca acttcttcct tggctacccc 240
cctgaaaatg tcacctgcct tgcatggacg aactcacagg caggaatggg ttggcttggg 300
tggggacatc ctgcaggttc caccctcatg ttggttcatc ttcaacattg tactgacttc 360
ttcccacttg acattcctca aggtcctgtg atcatggctg ggtctagtga ggttcaaacc 420
tgcactgccc tacccacacc cacacccagc tcagcgtcag tcaggatcaa caattaccta 480
gagatcatct ttctggggct taagcattgg tgggagcaga tgggatatga gctggggatt 540
tgggaatggg ggaagatatc tgctccccct ccccctacac cctagccttt taaaaggcct 600
tctcaggtca gagaccagga gaaaagtata ggagagatac acaatggacc aggaagaaga 660
aaagggagag ggaggctcag accttctaga caaggtaaga gggctctggc tgactccacc 720
atccgcttct tgaggtctcg gcacctgtaa ttgacaagat taattcattt atagggcatc 780
```

-continued

| | |
|---|---|
| taattagcaa gcaagtctct ggagtccect gacccagtta ctataacaca caggggggtat | 840 |
| aggtaggaga gtataagagc ccctcctcag ggcaaatgaa tggattctta gtactgtccc | 900 |
| ccaagagata gtaggtacta ggatttaggg gcacttctga gccccatttc cctggtaagt | 960 |
| gtcccaaccc cccaaatcaa cccaagcctg gtctcaatct aggacagtgg tagaatgctg | 1020 |
| tccctagagt cagtaccatg tgaaattgtg ctgcaggcag gggcccagg ctgggaggtg | 1080 |
| ggggttgggg gagtcagggc aggtcaggga aggagactca ggtttcattt agagaaattc | 1140 |
| tgcagacccg tgaggactat ggtgagagca gagatgggaa ggcaggcact gtttcgggtg | 1200 |
| gatgctgtct ggaagacagg gaaggcacag accaaactaa accaatcacg tctgtcccca | 1260 |
| aggcaggttc accggaccag gaaggcttct tcaacctgct gacccacgtg cagggcgatc | 1320 |
| gg | 1322 |

<210> SEQ ID NO 4
<211> LENGTH: 1006
<212> TYPE: DNA
<213> ORGANISM: Mus musculus
<220> FEATURE:
<223> OTHER INFORMATION: L7-4

<400> SEQUENCE: 4

| | |
|---|---|
| gttccaccct catgttggtt catcttcaac attgtactga cttcttccca cttgacattc | 60 |
| ctcaaggtcc tgtgatcatg gctgggtcta gtgaggttca aacctgcact gccctaccca | 120 |
| cacccacacc cagctcagcg tcagtcagga tcaacaatta cctagagatc atctttctgg | 180 |
| ggcttaagca ttggtgggag cagatgggat atgagctggg gatttgggaa tgggggaaga | 240 |
| tatctgctcc ccctcccct acaccctagc cttttaaaag gccttctcag gtcagagacc | 300 |
| aggagaaaag tataggagag atacacaatg gaccaggaag aagaaaaggg agagggaggc | 360 |
| tcagaccttc tagacaaggt aagagggctc tggctgactc caccatccgc ttcttgaggt | 420 |
| ctcggcacct gtaattgaca agattaattc atttataggg catctaatta gcaagcaagt | 480 |
| ctctggagtc ccctgaccca gttactataa cacacagggg gtataggtag gagagtataa | 540 |
| gagcccctcc tcagggcaaa tgaatggatt cttagtactg tccccaagaa gatagtaggt | 600 |
| actaggattt aggggcactt ctgagcccca tttccctggt aagtgtccca accccccaaa | 660 |
| tcaacccaag cctggtctca atctaggaca gtggtagaat gctgtcccta gagtcagtac | 720 |
| catgtgaaat tgtgctgcag gcaggggccc caggctggga ggtgggggtt gggggagtca | 780 |
| gggcaggtca gggaaggaga ctcaggtttc atttagagaa attctgcaga cccgtgagga | 840 |
| ctatggtgag agcagagatg gaaggcagg cactgtttcg ggtggatgct gtctggaaga | 900 |
| cagggaaggc acagaccaaa ctaaaccaat cacgtctgtc cccaaggcag gttcaccgga | 960 |
| ccaggaaggc ttcttcaacc tgctgaccca cgtgcagggc gatcgg | 1006 |

<210> SEQ ID NO 5
<211> LENGTH: 690
<212> TYPE: DNA
<213> ORGANISM: Mus musculus
<220> FEATURE:
<223> OTHER INFORMATION: L7-5

<400> SEQUENCE: 5

| | |
|---|---|
| tcagagcatg gtcagaaagc cacagctcat caatgaaatg gtcagggact tcctgtcctg | 60 |
| ctccatgcat aaatgaaaga cgaagacaac tcaaattggc atttgagggg cagataaaca | 120 |
| ggagcatccg gtagtttcac aggtggtcgg gtagcaggag ccgggttggt tggttggtct | 180 |

```
gtggagagtg cagggattaa gggaagaggc ctggacccca acttcttcct tggctacccc    240
cctgaaaatg tcacctgcct tgcatggacg aactcacagg caggaatggg ttggcttggg    300
tggggacatc ctgcaggttc caccctcatg ttggttcatc ttcaacattg tactgacttc    360
ttcccacttg acattcctca aggtcctgtg atcatggctg ggtctagtga ggttcaaacc    420
tgcactgccc tacccacacc cacacccagc tcagcgtcag tcaggatcaa caattaccta    480
gagatcatct ttctggggct taagcattgg tgggagcaga tgggatatga gctgggattt    540 gggaatggg ggaagatatc tgctccccct cccctacac cctagccttt aaaaggcct     600 tctcaggtca gagaccagga gaaagtata ggagagatac acaatggacc aggaagaaga   660
aaagggagag ggaggctcag accttctaga                                    690

<210> SEQ ID NO 6
<211> LENGTH: 375
<212> TYPE: DNA
<213> ORGANISM: Mus musculus
<220> FEATURE:
<223> OTHER INFORMATION: L7-6

<400> SEQUENCE: 6
gttccaccct catgttggtt catcttcaac attgtactga cttcttccca cttgacattc    60
ctcaaggtcc tgtgatcatg gctgggtcta gtgaggttca aacctgcact gccctaccca   120
cacccacacc cagctcagcg tcagtcagga tcaacaatta cctagagatc atctttctgg   180
ggcttaagca ttggtgggag cagatgggat atgagctggg gatttgggaa tgggggaaga   240
tatctgctcc ccctcccct acaccctagc cttttaaaag gccttctcag gtcagagacc   300
aggagaaaag tataggagag atacacaatg gaccaggaag aagaaaaggg agagggaggc   360
tcagaccttc tagac                                                    375

<210> SEQ ID NO 7
<211> LENGTH: 505
<212> TYPE: DNA
<213> ORGANISM: Mus musculus
<220> FEATURE:
<223> OTHER INFORMATION: L7-7

<400> SEQUENCE: 7
tactataaca cacaggggt ataggtagga gagtataaga gccctcctc agggcaaatg      60 aatggattct tagtactgtc ccccaagaga tagtaggtac taggatttag gggcacttct   120
gagccccatt tccctggtaa gtgtcccaac ccccaaatc aacccaagcc tggtctcaat    180
ctaggacagt ggtagaatgc tgtccctaga gtcagtacca tgtgaaattg tgctgcaggc   240
agggccccca ggctgggagg tggggttgg gggagtcagg ggcaggtcag ggaaggagac    300
tcaggtttca tttagagaaa ttctgcagac ccgtgaggac tatggtgaga gcagagatgg   360
gaaggcaggc actgtttcgg gtggatgctg tctggaagac agggaaggca cagaccaaac   420
taaaccaatc acgtctgtcc ccaaggcagg ttcaccggac caggaaggct tcttcaacct   480
gctgacccac gtgcagggcg atcgg                                         505

<210> SEQ ID NO 8
<211> LENGTH: 7399
<212> TYPE: DNA
<213> ORGANISM: Artificial Sequence
<220> FEATURE:
<223> OTHER INFORMATION: Synthetic Construct; pCL20c L7-4-GFP
```

```
<400> SEQUENCE: 8
gtcgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggact atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atgggaggcg tggcctgggc gggactgggg agtggcgagc     420
cctcagatcc tgcatataag cagctgcttt tgcctgtac tgggtctctc tggttagacc      480
agatctgagc ctgggagctc tctggctaac tagggaaccc actgcttaag cctcaataaa     540
gcttgccttg agtgcttcaa gtagtgtgtg cccgtctgtt gtgtgactct ggtaactaga     600
gatccctcag accctttag tcagtgtgga aaatctctag cagtggcgcc cgaacaggga      660
cttgaaagcg aaagggaaac cagaggagct ctctcgacgc aggactcggc ttgctgaagc     720
gcgcacggca agaggcgagg ggcggcgact ggtgagtacg ccaaaaattt tgactagcgg     780
aggctagaag gagagagatg ggtgcgagag cgtcagtatt aagcggggga gaattagatc     840
gcgatgggaa aaaattcggt taaggccagg gggaagaaaa aatataaat taaaacatat      900
agtatgggca agcaggagc tagaacgatt cgcagttaat cctggcctgt tagaaacatc      960
agaaggctgt agacaaatac tgggacagct acaaccatcc cttcagacag gatcagaaga    1020
acttagatca ttatataata cagtagcaac cctctattgt gtgcatcaaa ggatagagat    1080
aaaagacacc aaggaagctt tagacaagat agaggaagag caaaacaaaa gtaagaaaaa    1140
agcacagcaa gcagcaggat cttcagacct ggaaattccc tacaatcccc aaagtcaagg    1200
agtagtagaa tctatgaata aagaattaaa gaaaattata ggacaggtaa gagatcaggc    1260
tgaacatctt aagacagcag tacaaatggc agtattcatc cacaatttta aaagaaaagg    1320
ggggattggg gggtacagtg caggggaaag aatagtagac ataatagcaa cagacataca    1380
aactaaagaa ttacaaaaac aaattacaaa aattcaaaat tttcgggttt attacaggga    1440
cagcagaaat ccactttgga aaggaccagc aaagctcctc tggaaaggtg aagggcagt     1500
agtaatacaa gataatagtg acataaaagt agtgccaaga agaaaagcaa agatcattag    1560
ggattatgga aaacagatgg caggtgatga ttgtgtggca agtagacagg atgaggatta    1620
gaacatggaa aagtttagta aaacaccata aggaggagat atgagggaca attggagaag    1680
tgaattatat aaatataaag tagtaaaaat tgaaccatta ggagtagcac ccaccaaggc    1740
aaagagaaga gtggtgcaga gagaaaaaag agcagtggga ataggagctt tgttccttgg    1800
gttcttggga gcagcaggaa gcactatggg cgcagcgtca atgacgctga cggtacaggc    1860
cagacaatta ttgtctggta tagtgcagca gcagaacaat ttgctgaggg ctattgaggc    1920
gcaacagcat ctgttgcaac tcacagtctg ggcatcaag cagctccagg caagaatcct    1980
ggctgtggaa agatacctaa aggatcaaca gctcctgggg atttggggtt gctctggaaa    2040
actcatttgc accactgctg tgccttggaa tgctagttgg agtaataaat ctctggaaca    2100
gatttggaat cacacgacct ggatggagtg ggacagagaa attaacaatt acacaagctt    2160
aatacactcc ttaattgaag aatcgcaaaa ccagcaagaa aagaatgaac aagaattatt    2220
ggaattagat aaatgggcaa gtttgtgaa ttggtttaac ataacaaatt ggctgtggta     2280
tataaaatta ttcataatga tagtaggagg cttggtaggt ttaagaatag tttttgctgt    2340
```

```
actttctata gtgaatagag ttaggcaggg atattcacca ttatcgtttc agacccacct      2400
cccaaccccg aggggaccga gctcaagctt cgaacgcgtg gttccaccct catgttggtt      2460
catcttcaac attgtactga cttcttccca cttgacattc ctcaaggtcc tgtgatcatg      2520
gctgggtcta gtgaggttca aacctgcact gccctaccca cacccacacc cagctcagcg      2580
tcagtcagga tcaacaatta cctagagatc atctttctgg ggcttaagca ttggtgggag      2640
cagatgggat atgagctggg gatttgggaa tgggggaaga tatctgctcc ccctcccect      2700 acaccctagc cttttaaaag gccttctcag gtcagagacc aggagaaaag tataggagag      2760
atacacaatg gaccaggaag aagaaaaggg agagggaggc tcagaccttc tagacaaggt      2820
aagagggctc tggctgactc caccatccgc ttcttgaggt ctcggcacct gtaattgaca      2880
agattaattc atttataggg catctaatta gcaagcaagt ctctggagtc ccctgaccca      2940
gttactataa cacacagggg gtataggtag gagagtataa gagcccctcc tcagggcaaa      3000
tgaatggatt cttagtactg tcccccaaga gatagtaggt actaggattt aggggcactt      3060
ctgagcccca tttccctggt aagtgtccca acccccaaa tcaacccaag cctggtctca      3120
atctaggaca gtggtagaat gctgtcccta gagtcagtac catgtgaaat tgtgctgcag      3180 gcagggccc caggctggga ggtgggggtt gggggagtca gggcaggtca gggaaggaga      3240
ctcaggtttc atttagagaa attctgcaga cccgtgagga ctatggtgag agcagagatg      3300
ggaaggcagg cactgtttcg ggtggatgct gtctggaaga cagggaaggc acagaccaaa      3360
ctaaaccaat cacgtctgtc cccaaggcag gttcaccgga ccaggaaggc ttcttcaacc      3420
tgctgaccca cgtgcagggc gatcgggaat tcatggtgag caagggcgag gagctgttca      3480
ccggggtggt gcccatcctg gtcgagctgg acggcgacgt aaacggccac aagttcagcg      3540
tgtccggcga gggcgagggc gatgccacct acggcaagct gaccctgaag ttcatctgca      3600
ccaccggcaa gctgcccgtg ccctggccca ccctcgtgac caccctgacc tacggcgtgc      3660
agtgcttcag ccgctacccc gaccacatga agcagcacga cttcttcaag tccgccatgc      3720
ccgaaggcta cgtccaggag cgcaccatct tcttcaagga cgacggcaac tacaagaccc      3780
gcgccgaggt gaagttcgag ggcgacaccc tggtgaaccg catcgagctg aagggcatcg      3840
acttcaagga ggacggcaac atcctggggc acaagctgga gtacaactac aacagccaca      3900
acgtctatat catggccgac aagcagaaga acggcatcaa ggtgaacttc aagatccgcc      3960
acaacatcga ggacggcagc gtgcagctcg ccgaccacta ccagcagaac ccccatcg      4020 gcgacggccc cgtgctgctg cccgacaacc actacctgag cacccagtcc gccctgagca      4080
aagaccccaa cgagaagcgc gatcacatgg tcctgctgga gttcgtgacc gccgccggga      4140
tcactctcgg catggacgag ctgtacaagt aagcggccgc atcgatgccg tatacggtac      4200
ctttaagacc aatgacttac aaggcagctg tagatcttag ccactttta aaagaaaagg      4260 ggggactgga agggctaatt cactcccaaa gaagacaaga tctgctttt gcctgtactg      4320 ggtctctctg gttagaccag atctgagcct gggagctctc tggctaacta gggaacccac      4380
tgcttaagcc tcaataaagc ttcagctgct cgagctagca gatctttttc cctctgccaa      4440
aaattatggg gacatcatga agccccttga gcatctgact tctggctaat aaaggaaatt      4500
tattttcatt gcaatagtgt gttggaattt tttgtgtctc tcactcggaa ggacatatgg      4560
gagggcaaat catttaaaac atcagaatga gtatttggtt tagagtttgg caacatatgc      4620
catatgctgg ctgccatgaa caaaggtggc tataaagagg tcatcagtat atgaaacagc      4680
```

```
cccctgctgt ccattcctta ttccatagaa aagccttgac ttgaggttag attttttta   4740
tattttgttt tgtgttattt ttttctttaa catccctaaa attttccttt catgttttac   4800
tagccagatt tttcctcctc tcctgactac tcccagtcat agctgtccct cttctcttat   4860
gaagatccct cgacctgcag cccaagcttg gcgtaatcat ggtcatagct gtttcctgtg   4920
tgaaattgtt atccgctcac aattccacac aacatacgag ccggaagcat aaagtgtaaa   4980
gcctggggtg cctaatgagt gagctaactc acattaattg cgttgcgctc actgcccgct   5040
ttccagtcgg gaaacctgtc gtgccagcgg atccgcatct caattagtca gcaaccatag   5100
tcccgcccct aactccgccc atcccgcccc taactccgcc cagttccgcc cattctccgc   5160
cccatggctg actaattttt tttatttatg cagaggccga ggccgcctcg gcctctgagc   5220
tattccagaa gtagtgagga ggcttttttg gaggcctagg cttttgcaaa aagctaactt   5280
gtttattgca gcttataatg gttacaaata aagcaatagc atcacaaatt tcacaaataa   5340
agcattttt tcactgcatt ctagttgtgg tttgtccaaa ctcatcaatg tatcttatca   5400
tgtctggatc cgctgcatta atgaatcggc caacgcgcgg ggagaggcgg tttgcgtatt   5460
gggcgctctt ccgcttcctc gctcactgac tcgctgcgct cggtcgttcg gctgcggcga   5520
gcggtatcag ctcactcaaa ggcggtaata cggttatcca cagaatcagg ggataacgca   5580
ggaaagaaca tgtgagcaaa aggccagcaa aaggccagga accgtaaaaa ggccgcgttg   5640
ctggcgtttt tccataggct ccgcccccct gacgagcatc acaaaaatcg acgctcaagt   5700
cagaggtggc gaaacccgac aggactataa agataccagg cgtttccccc tggaagctcc   5760
ctcgtgcgct ctcctgttcc gaccctgccg cttaccggat acctgtccgc ctttctccct   5820
tcgggaagcg tggcgctttc tcaatgctca cgctgtaggt atctcagttc ggtgtaggtc   5880
gttcgctcca agctgggctg tgtgcacgaa ccccccgttc agcccgaccg ctgcgcctta   5940
tccggtaact atcgtcttga gtccaacccg gtaagacacg acttatcgcc actggcagca   6000
gccactggta acaggattag cagagcgagg tatgtaggcg gtgctacaga gttcttgaag   6060
tggtggccta actacggcta cactagaagg acagtatttg gtatctgcgc tctgctgaag   6120
ccagttacct tcggaaaaag agttggtagc tcttgatccg gcaaacaaac caccgctggt   6180
agcggtggtt tttttgtttg caagcagcag attacgcgca gaaaaaaagg atctcaagaa   6240
gatcctttga tcttttctac ggggtctgac gctcagtgga acgaaaactc acgttaaggg   6300
attttggtca tgagattatc aaaaaggatc ttcacctaga tccttttaaa ttaaaaatga   6360
agttttaaat caatctaaag tatatatgag taaacttggt ctgacagtta ccaatgctta   6420
atcagtgagg cacctatctc agcgatctgt ctatttcgtt catccatagt tgcctgactc   6480
cccgtcgtgt agataactac gatacgggag ggcttaccat ctggccccag tgctgcaatg   6540
ataccgcgag acccacgctc accggctcca gatttatcag caataaacca gccagccgga   6600
agggccgagc gcagaagtgg tcctgcaact ttatccgcct ccatccagtc tattaattgt   6660
tgccgggaag ctagagtaag tagttcgcca gttaatagtt tgcgcaacgt tgttgccatt   6720
gctacaggca tcgtggtgtc acgctcgtcg tttggtatgg cttcattcag ctccggttcc   6780
caacgatcaa ggcgagttac atgatccccc atgttgtgca aaaaagcggt tagctccttc   6840
ggtcctccga tcgttgtcag aagtaagttg gccgcagtgt tatcactcat ggttatggca   6900
gcactgcata attctcttac tgtcatgcca tccgtaagat gcttttctgt gactggtgag   6960
tactcaacca agtcattctg agaatagtgt atgcggcgac cgagttgctc ttgcccggcg   7020
tcaatacggg ataataccgc gccacatagc agaactttaa aagtgctcat cattggaaaa   7080
```

```
cgttcttcgg ggcgaaaact ctcaaggatc ttaccgctgt tgagatccag ttcgatgtaa    7140
cccactcgtg cacccaactg atcttcagca tcttttactt tcaccagcgt ttctgggtga    7200
gcaaaaacag gaaggcaaaa tgccgcaaaa aagggaataa gggcgacacg gaaatgttga    7260
atactcatac tcttcctttt tcaatattat tgaagcattt atcagggtta ttgtctcatg    7320
agcggataca tatttgaatg tatttagaaa aataaacaaa taggggttcc gcgcacattt    7380
ccccgaaaag tgccacctg                                                  7399

<210> SEQ ID NO 9
<211> LENGTH: 27
<212> TYPE: DNA
<213> ORGANISM: Artificial Sequence
<220> FEATURE:
<223> OTHER INFORMATION: Synthetic Construct; primer

<400> SEQUENCE: 9
atgagggaca attggagaag tgaatta                                         27

<210> SEQ ID NO 10
<211> LENGTH: 27
<212> TYPE: DNA
<213> ORGANISM: Artificial Sequence
<220> FEATURE:
<223> OTHER INFORMATION: Synthetic Construct; primer

<400> SEQUENCE: 10
cagactgtga gttgcaacag atgctgt                                         27
```